(12) United States Patent
Wishart et al.

(10) Patent No.: US 10,562,863 B2
(45) Date of Patent: Feb. 18, 2020

(54) HETEROBIFUNCTIONAL LINKER

(71) Applicant: THE GOVERNORS OF THE UNIVERSITY OF ALBERTA, Edmonton (CA)

(72) Inventors: David Scott Wishart, Edmonton (CA); Khalid Azyat, Edmonton (CA); Daniel Golec, Edmonton (CA)

(73) Assignee: THE GOVERNORS OF THE UNIVERSITY OF ALBERTA, Edmonton (CA)

( * ) Notice: Subject to any disclaimer, the term of this patent is extended or adjusted under 35 U.S.C. 154(b) by 0 days.

(21) Appl. No.: 15/713,285

(22) Filed: Sep. 22, 2017

(65) Prior Publication Data

US 2018/0086724 A1 Mar. 29, 2018

Related U.S. Application Data

(60) Provisional application No. 62/399,114, filed on Sep. 23, 2016.

(30) Foreign Application Priority Data

Sep. 23, 2016 (CA) .................................. 2943103

(51) Int. Cl.
*C07D 249/04* (2006.01)
(52) U.S. Cl.
CPC .................................. *C07D 249/04* (2013.01)
(58) Field of Classification Search
None
See application file for complete search history.

(56) References Cited

PUBLICATIONS

STN Registry database entry for CAS RN 552855-26-2, STN entry date Jul. 23, 2003; Accessed Jul. 9, 2018.*
STN Registry database entry for CAS RN 1221294-24-1, STN entry date May 4, 2010; Accessed Jul. 9, 2018.*
Li et al., Bioorganic & Medicinal Chemistry Letters, vol. 15, No. 24, Dec. 15, 2005, pp. 5558-5561.*
Abdel-Magid et al., "Reductive Amination of Aldehydes and Ketones with Sodium Triacetoxyborohydride. Studies on Direct and Indirect Reductive Amination Procedures(1)," Journal of Organic Chemistry, May 1996, vol. 61 (11), pp. 3849-3862.
Adams et al., "Nucleotide Sequence and Genetic Characterization Reveal Six Essential Genes for the LIV-I and LS Transport Systems of *Escherichia coli*," Journal of Biological Chemistry, Jul. 1990, vol. 265 (20), pp. 11436-11443.
Agasti et al., "Nanoparticles for Detection and Diagnosis," Advanced Drug Delivery Reviews, Mar. 2010, vol. 62 (3), pp. 316-328.
Alzheimer's Association., "2014 Alzheimer's Disease Facts and Figures," Alzheimer's & Dementia, Mar. 2014, vol. 10 (2), pp. e47-e92.
Baranov et al., "Synthesis and Characterization of Azidoalkyl-Functionalized Gold Nanoparticles as Scaffolds for "Click"—Chemistry Derivatization," Journal of Materials Chemistry, Apr. 2011, vol. 21, pp. 6152-6157.
Bishop et al., "(Iodoacetamido)Fluorescein Labels a Pair of Proximal Cysteines on the Ca2+-ATPase of Sarcoplasmic Reticulum," Biochemistry, Jul. 1988, vol. 27 (14), pp. 5233-5240.
Boisselier et al., "How to Very Efficiently Functionalize Gold Nanoparticles by "Click" Chemistry," Chemical Communications, Nov. 2008, vol. 44, pp. 5788-5790.
Bowden et al., "Folding and Aggregation of Beta-lactamase in the Periplasmic Space of *Escherichia coli*," Journal of Biological Chemistry, Oct. 1990, vol. 265 (28), pp. 16760-16766.
Burrage et al., "Branched-Chain Amino Acid Metabolism: From Rare Mendelian Diseases to More Common Disorders," Human Molecular Genetics, Sep. 2014, vol. 23 (R1), pp. R1-R8.
Cadle et al., "Cellular Phone-Based Image Acquisition and Quantitative Ratiometric Method for Detecting Cocaine and Benzoylecgonine for Biological and Forensic Applications," Substance Abuse, Sep. 2010, pp. 21-33.
Carrio et al., "Automated Low-Cost Smartphone-Based Lateral Flow Saliva Test Reader for Drugs-of-Abuse Detection," Sensors, Nov. 2015, vol. 15 (11), pp. 29569-29593.
Fonteh et al., "Free Amino Acid and Dipeptide Changes in the Body Fluids From Alzheimer's Disease Subjects," Amino Acids, Feb. 2007, vol. 32 (2), pp. 213-224.
Fracchiolla et al., "Biosensors in Clinical Practice: Focus on Oncohematology," Sensors (Basel), May 2013, vol. 13 (5), pp. 6423-6447.
Gold Nanoparticles: Properties and Applications | Sigma-Aldrich https://www.sigmaaldrich.com/technical-documents/articles/materials-science/nanomaterials/gold-nanoparticles.html, retrieved online Dec. 22, 2017.
Herrou et al., "Myo-Inositol and D-Ribose Ligand Discrimination in an ABC Periplasmic Binding Protein," Journal of Bacteriology, May 2013, vol. 195 (10), pp. 2379-2388.
Hwang et al., "Application of a SERS-Based Lateral Flow Immunoassay Strip for the Rapid and Sensitive Detection of Staphylococcal Enterotoxin B," Nanoscale, Jun. 2016, vol. 8 (22), pp. 11418-11425.
Jain., "Current Status of Molecular Biosensors," Medical Device Technologies, May 2003, vol. 14 (4), pp. 10-15.
Kay., "mHealth: New Horizons for Health Through Mobile Technologies," GSMA mHA Mobile Health Summit, World Health Organization, Jun. 2011, 21 pages.
Kolb et al., "Click Chemistry: Diverse Chemical Function from a Few Good Reactions," Angewandte Chemie International Edition English, Jun. 2001, vol. 40 (11), pp. 2004-2021.
Koulman et al., "From Differentiating Metabolites to Biomarkers," Analytical and Bioanalytical Chemistry, Jun. 2009, vol. 394 (3), pp. 663-670.
Lai et al., "Improving Lateral-Flow Immunoassay (LFIA) Diagnostics Via Biomarker Enrichment for mHealth," Methods in Molecular Biology, Jan. 2015, vol. 1256, pp. 71-84.
Lee et al., "Selection of Human Antibody Fragments by Phage Display," Nature Protocols, Nov. 2007, vol. 2, pp. 3001-3008.
Liu et al., "Lateral Flow Immunochromatographic Assay for Sensitive Pesticide Detection by Using Fe3O4 Nanoparticle Aggregates as Color Reagents," Analytical Chemistry, Sep. 2011, vol. 83 (17), pp. 6778-6784.

(Continued)

*Primary Examiner* — Alicia L Otton
(74) *Attorney, Agent, or Firm* — Borden Ladner Gervais LLP

(57) ABSTRACT

The present disclosure relates generally to heterobifunctional linkers.

4 Claims, 35 Drawing Sheets

(56) References Cited

PUBLICATIONS

Lund et al., "The Influence of Ligand Organization on the Rate of Uptake of Gold Nanoparticles by Colorectal Cancer Cells," Biomaterials, Dec. 2011, vol. 32 (36), pp. 9776-9784.

Ngom et al., "Development and Application of Lateral Flow Test Strip Technology for Detection of Infectious Agents and Chemical Contaminants: A Review.," Analytical and Bioanalytical Chemistry, Jun. 2010, vol. 397 (3), pp. 1113-1135.

Ojea-Jiménez et al., "Facile Preparation of Cationic Gold Nanoparticle-Bioconjugates for Cell Penetration and Nuclear Targeting," ACS Nano, Aug. 2012, vol. 6 (9), pp. 7692-7702.

Posthuma-Trumpie et al., "Lateral Flow (Immuno)Assay: Its Strengths, Weaknesses, Opportunities and Threats. A Literature Survey," Analytical and Bioanalytical Chemistry, Jan. 2009, vol. 393 (2), pp. 569-582.

Rachakonda et al., "Biomarkers of Neurodegenerative Disorders: How Good Are They?," Cell Research, Oct. 2004, vol. 14 (5), pp. 349-358.

Rosen., "Market Trends in Lateral Flow Immunoassays," Lateral Flow Immunoassay; Humana Press: Totowa, NJ, Jan. 2009.

Saha et al., "Gold Nanoparticles in Chemical and Biological Sensing," Chemical Reviews, May 2012, vol. 112 (5), pp. 2739-2779.

Schulz et al., "Effect of the Spacer Structure on the Stability of Gold Nanoparticles Functionalized With Monodentate Thiolated Poly(Ethylene Glycol) Ligands," Langmuir, Aug. 2013, vol. 29 (31), pp. 9897-9908.

Shukla et al., "Biocompatibility of Gold Nanoparticles and Their Endocytotic Fate Inside the Cellular Compartment: A Microscopic Overview," Langmuir, Nov. 2005, vol. 21 (23), pp. 10644-10654.

Singh et al., "Synthesis and Characterization of Hapten-Protein Conjugates for Antibody Production Against Small Molecules," Bioconjugate Chemistry, Jan. 2004, vol. 15 (1), pp. 168-173.

Smet et al., "Synthesis of Crown Ethers Containing a Rubicene Moiety," Molecules, Mar. 2000, vol. 5 (3), pp. 620-628.

Spyrou et al., "Digital Camera and Smartphone as Detectors in Paper-Based Chemiluminometric Genotyping of Single Nucleotide Polymorphisms," Analytical and Bioanalytical Chemistry, Oct. 2016, vol. 408 (26), pp. 7393-7402.

Tang et al., "Magnetic Nanogold Microspheres-Based Lateral-Flow Immunodipstick for Rapid Detection of Aflatoxin B2 in Food," Biosensors and Bioelectronics, Oct. 2009, vol. 25 (2), pp. 514-518.

Taranova et al., "Integration of Lateral Flow and Microarray Technologies for Multiplex Immunoassay: Application to the Determination of Drugs of Abuse," Microchimica Acta, Aug. 2013, vol. 180, pp. 1165-1172.

Turkevich et al., "A Study of the Nucleation and Growth Processes in the Synthesis of Colloidal Gold," Discussions of the Faraday Society, May 1951, vol. 11, p. 55.

Volkov et al., "Rapid Prototyping of Lateral Flow Assays," Methods in Molecular Biology, 2009, vol. 504, pp. 217-235.

Wang et al., "Glucose Biochip: Dual Analyte Response in Connection to Two Pre-column Enzymatic Reactions," Analyst, Aug. 2001, vol. 126 (8), pp. 1203-1206.

Willis et al., "Interactions of a Glutamate-Aspartate Binding Protein With the Glutamate Transport System of *Escherichia coli*," Journal of Biological Chemistry, Apr. 1975, vol. 250 (7), pp. 2581-2586.

Zakaria et al., "Small Molecule—and Amino Acid-induced Aggregation of Gold Nanoparticles," Langmuir, Jun. 2013, vol. 29 (25), pp. 7661-7673.

Zhang et al., "Development of an Immunochromatographic Lateral Flow Test Strip for Detection of Beta-Adrenergic Agonist Clenbuterol Residues," Journal of Immunological Methods, May 2006, vol. 312 (1-2), pp. 27-33.

Zhao et al., "How a Simple "Clicked" Pegylated 1,2,3-triazole Ligand Stabilizes Gold Nanoparticles for Multiple Usage," Chemical Communications, Apr. 2013, vol. 49 (31), pp. 3218-3220.

Zhong et al., "The Surface Chemistry of Au Colloids and Their Interactions with Functional Amino Acids," Journal of Physical Chemistry B, Mar. 2004, vol. 108 (13), pp. 4046-4052.

\* cited by examiner

Compound 10(Glutamate - Linker 1) ($^1$H) (CD$_3$OD)

Compound 11 (Carnosine - Linker 1) ($^1$H) (CD$_3$OD)

Compound 11 (Carnosine - Linker 1) ($^{13}$C) (CD$_3$OD)

12 (Histidine - Linker 1) ($^1$H) (CD$_3$OD)

12 (Histidine - Linker 1) ($^{13}$C) (CD$_3$OD)

_US 10,562,863 B2_

HETEROBIFUNCTIONAL LINKER

CROSS-REFERENCE TO RELATED APPLICATIONS

This application claims the benefit of priority to U.S. 62/399,114, filed Sep. 23, 2016, and Canadian Patent Application number 2,943,103, filed Sep. 23, 2016, the entire contents all of which is hereby incorporated by reference.

FIELD

The present disclosure relates generally to heterobifunctional linkers.

BACKGROUND

The identification and quantification of analytes (e.g., metabolites) typically requires access to large and expensive instrumentation, such as NMR and mass spectrometers.

Some molecules (like glucose) can be detected via enzymatic assays while others, like vitamin D or certain pesticides, can be detected through immunological methods using chemo-conjugated proteins. However, these low-cost assays are very compound specific, and can take years of trial-and-error to develop.

Metabolomics is a relatively new branch of 'omics science that involves the comprehensive characterization of large numbers of metabolites in cells, tissues and biofluids. Over the past 10 years, interest in metabolomics has grown tremendously. This is because it offers biologists and other life scientists a rapid and effective means to chemically phenotype organisms. It also offers physicians and clinicians a very quick and efficient route to discover or test for disease biomarkers.[1-4] Most metabolomic assays involve the use of classical separation technologies such as liquid chromatography or gas chromatography. These are normally coupled with high-end chemical detection instruments such as NMR or mass spectrometers to identify and quantify metabolites from biological samples. The size, sophistication and expense of most metabolomics instruments means that many metabolomics activities must be conducted in well-equipped, multi-million dollar core facilities. The requirement for expensive instruments and highly trained personnel has made metabolomics increasingly inaccessible to many life scientists. Ideally what is missing is a novel approach that "democratizes" metabolomics by making metabolomics assays portable, simple and inexpensive. One way of doing this is to use the power of enzyme or protein-based assays to detect metabolites. Perhaps one of the best known examples of a portable enzyme-based metabolite assay is the blood glucose sensor.[5,6] This assay, which uses glucose oxidase as a dual sensor/detector is used by millions of diabetics world-wide.

However, very few enzyme/metabolite systems exist that can generate easy-to-detect signals. Indeed, most of these enzyme/metabolite detection systems require an enzyme that uses a colorimetric cofactor (NADP for instance) or a detectable redox couple (glucose oxidase for instance). Only a small number of enzymatic reactions, including glucose oxidation via glucose oxidase, fit these requirements.[7]

The preparation of small molecule-protein conjugates is difficult. Often, chemically modified versions of the analyte must be prepared and various trial-and-error attempts must be performed to develop an optimal analyte analog and to chemically couple that analyte to the protein of choice.[14] Difficulties often arise due to inconsistent orientation, placement and abundance of the analyte on the protein surface. Once coupled, an appropriate antibody to the protein bound molecule must be developed; small molecules alone cannot be used to raise antibodies. The resulting protein-hapten antibodies may or may not recognize the pure small molecule, and for the case of metabolites, autoimmunity would pose a problem, leading to more trial and error attempts to create optimal antibodies that recognize both forms. As a result, years of effort must be devoted to generate a useful small-molecule analyte immunoassay. These compound-specific challenges along with the difficulty in preparing appropriate protein conjugates, appropriate colorimetric amplification techniques and appropriate small molecule antibodies have led to a rather modest number of small molecule immunoassays being developed. Only a few different small molecule analyte assays that have been described in the literature or that have reached the market.[15,16] This is in contrast to the thousands of protein-based ELISAs that have already been described or developed. Clearly, if small molecule immunoassays are ever to have an impact on metabolomics—where dozens to hundreds of molecules need to be detected—there will need to be a significant improvement in their rate or ease of development.

Presently, there is a lack of a general method that would both simplify the process and shorten the assay development time for small molecule detection.

SUMMARY

In a one aspect the present disclosure provides a method of manufacture a of water soluble heterobifunctional linker (L1), comprising:

a. producing tetraethylene glycol (TEG) p-toluene sulfonate (5) by tosylation of tetraethylene glycol with p-tosylchloride;

b. producing tetraethylene glycol azide (6) by nucleophilic substitution of tetraethylene glycol p-toluene sulfonate (5) with sodium azide in DMF;

c. producing p-toluene sulfonate tetraethylene glycolazide (7) by tosylation of tetraethylene glycol azide (6);

d. producing azidetetraethylene glycol thioacetate (8) by nucleophilic substitution of p-toluene sulfonate tetraethylene glycolazide (7) with potassium thioacetate.

e. producing TEG-"Clicked"-Alcohol (9) by reaction of azidetetraethylene glycol thioacetate (8) with 4-pentyn-1-ol to form 1,4-disubstitued-1,2,3-triazole;

f. producing the soluble heterobifunctional linker (L1) by removing excess copper from the TEG-"Clicked"-Alcohol (9) in step (e) and oxidizing by swern oxidation.

In one aspect, there is described a method of producing an AuNP-L1-analyte conjugate of Formula I, $$\text{AuNP-L1-analyte} \qquad (I)$$

comprising:
reacting a heterobifunctional linker (L1) with the free amine function of an analyte and conjugating AuNP to the thiol group of the L1, to form the AuNP-L1-analyte conjugate.

In one aspect, there is described a method of producing a label-L1-analyte conjugate of Formula II, $$\text{label-L1-analyte} \qquad (II)$$

comprising:
reacting a heterobifunctional linker (L1) with the free amine function of an analyte and conjugating the label to the thiol group of the L1, to form the label-L1-analyte conjugate.

In one example, said analyte is an amino acid or a polypeptide.

In one example, the amino acid is glutamate or histidine.

In one example, said polypeptide is carnosine.

In one example, the AuNP is a stabilized colloid AuNP.

In one example, the stabilized colloid AuNP is produced by trisodium citrate ($Na_3C_6H_5O_7$) reduction of chloroauric acid (HAuCl4) to form gold nanoparticles In one aspect, the method further comprising a analyte reagent on the surface of the AuNPs.

In one example, said second analyte comprises an amino acid or polypeptide.

In one example, said amino acid is Leucine or Histidine.

In one example, said polypeptide is carnosine.

In one aspect there is described a method of selecting an antibody specific for an analyte, comprising: screening a library comprising antibodies for binding of an antibody within said library to a reagent-L1 conjugate.

In one example, said library comprises a library of single chain antibodies (scFv).

In one example, said analyte is an amino acid.

In one aspect there is described a method for detecting an analyte in a sample, comprising:

a. providing an analyte binding reagent on a substrate;

b. incubating an AuNP-L1-reagent conjugate with the substrate and a sample, wherein said AuNP-L1-analyte conjugate binds to said reagent binding reagent, c. detecting an amount of complex formed between said AuNP-L1-analyte conjugate and said metabolite binding reagent on said substrate, wherein a reduced amount of complex, optionally compared to a control, indicates the present of said analyte in said sample.

In one example, said metabolite binding analyte comprises a protein.

In one example, said AuNP-L1-analyte conjugate comprises an amino acid.

In one aspect there is provided an system for detecting a analyte in a sample, comprising: a substrate comprising a reagent binding analyte, and an AuNP-L1-analyte conjugate, In one aspect, there is provided a water soluble heterobifunctional linker produced according to the method of anyone of claims 1 to 4.

In one aspect, there is provided a water soluble heterobifunctional linker (L1) having the structure of Formula III:

A-B-C  (III)

wherein,

A is a thiol group;

B is a PEG linker moiety,

C is an aldehyde group.

T In one example, said thiol group is suitable for covalent attachment to a label.

In one example, said aldehyde group is suitable for covalent attachment to a primary amine group.

In one example, wherein said aldehyde group is connected to the PEG linker moiety through a triazole unit.

In one example, said primary amine group is a primary amine group on an amino acid.

In one example, the water soluble heterobifunctional linker (L1) is a compound of formula IIIa:

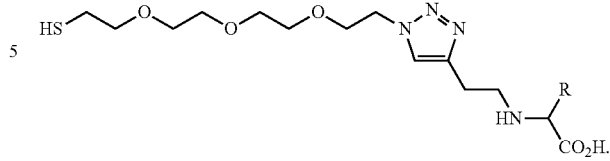

(IIIA)

In one example, the water soluble heterobifunctional linker (L1) is a compound of formula IIIb:

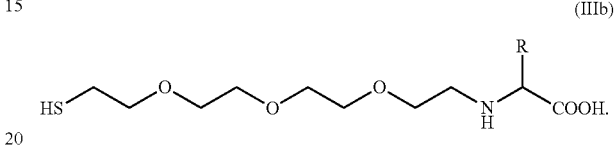

(IIIb)

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

FIG. 3A L1 (Aldehyde-Linker 1) (1H) ($CDCl_3$); FIG. 3B Compound 10(Glutamate-Linker 1) ($^1$H) ($CD_3OD$); FIG. 3C Compound 10 (Glutamate-Linker 1) ($^{13}$C) ($CD_3OD$); FIG. 3D Compound 11 (Carnosine-Linker 1) ($^1$H) ($CD_3OD$)); FIG. 3E Compound 11 (Carnosine-Linker 1) ($^{13}$C) ($CD_3OD$); FIG. 3F 12 (Histidine-Linker 1) (1H) ($CD_3OD$); FIG. 3G 12 (Histidine-Linker 1) ($^{13}$C) ($CD_3OD$).

FIG. 7A Au-citrate FIG. 7B 1 (Au-Glu-1) FIG. 7C 2 (Au-Glu-2) FIG. 7D 4 (Carn-1-Au-Glu-1) FIG. 7E 6 (Carn-2-Au-Glu-1) FIG. 7F 8 (Carn-1-Au-Glu-2) FIG. 7G 10 (Carn-2-Au-Glu-2) FIG. 7H 3 (His-1-Au-Glu-1) FIG. 7I 5 (His-2-Au-Glu-1) FIG. 7J 7 (His-1-Au-Glu-2 FIG. 7K 9 (His-2Au-Glu-2).

FIG. 8A Ile-L1-IAF m/z=819 peak 2, FIG. 8B Val-L1-IAF M/z=805 peak 4. Ion positive configuration used, shows compound as peak with +1 mass (820 m/z for A and 806 m/z for FIG. 8B.

FIG. 12 shows UV-Vis Spectra of double conjugated AuNPs with modified aminoacids-linker-1.

DETAILED DESCRIPTION

Figure 1:
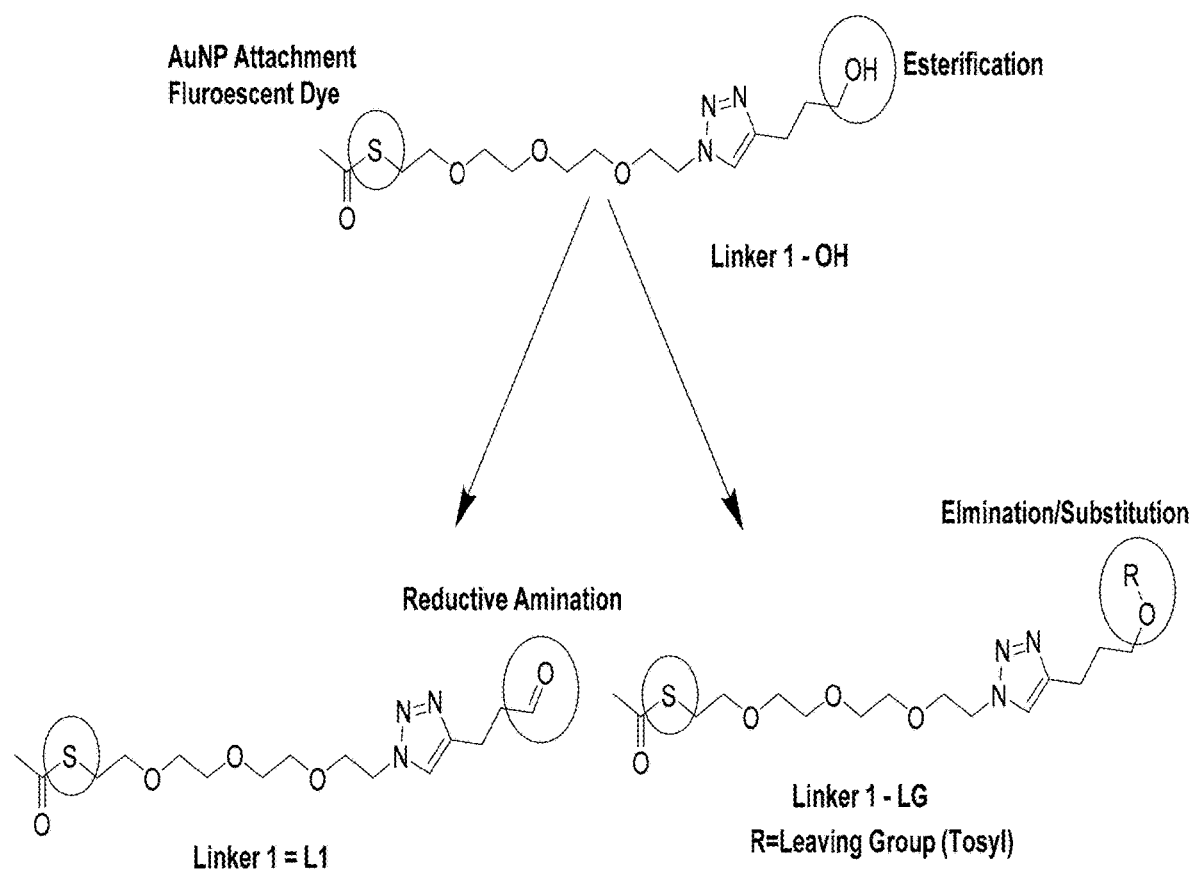
FIG. 1 depicts the chemical structure of Linker 1 (L1) and derivatives thereof. Metabolites may be conjugated through amino groups amination (left) or substitution (right). Exchange reactions on terminal thioester can attach the linker to AuNP

In one example, described herein is an approach that allows the facile preparation of metabolite conjugates that can be used for the selection of compound-specific antibodies or binding proteins and for the detection of metabolite-protein binding events using a wide range of detection technologies. We describe the synthesis of a water-soluble, heterobifunctional linker with a thiol group at one end and an aldehyde group on the other end. The thiol group can be used to covalently couple to a gold nanoparticle (AuNP) or a fluorophore, while the aldehyde group can be used to link to a primary amine group (e.g. amino acids). We demonstrate preparing conjugates of carnosine, histidine, glutamate and leucine, with the linker. We further show how these conjugated amino acids can be used to select for specific antibodies against metabolites, using phage display methods. By appropriately modifying the surface of gold nanoparticles and conjugating the modified amino acids to the AuNPs, stable, water-soluble gold colloids were prepared, decorated with specific amino acids. We also show how these amino acid-AuNPs can be used to detect metabolites using a competitive lateral flow assay.

In one aspect, described herein is a heterobifunctional reagent/linker that replaces the need for protein conjugation to connect an analyte to a signal generating molecule. In one aspect, described herein is a heterobifunctional reagent/linker that replaces the need for connecting the protein to the signal generating molecule with connecting the analyte to the signal generating molecule.

In one aspect, a heterobifunctional linker covalently binds to, for example, an analyte, such as small molecule of interest, at one end, while at the same time binding to a signal generating molecule (including but not limited to a gold nanoparticle, a fluorophore, an amplifying enzyme) or a column substrate (e.g., for affinity purification of an analyte-specific binding protein) at the other.

In one aspect, the heterobifunctional linker is water-soluble, flexible, and customizable (for different linking needs).

In one aspect, the heterobifunctional linker is compatible with linking different types of analytes (including but not limited to metabolites, peptides, proteins, carbohydrates, lipids) to different signal generating molecules (including but not limited to a gold nanoparticle, a fluorophore, an amplifying enzyme, a quantum dot, a radioactive label) or different column substrates (column matrices, polymers, other materials surfaces, such as gold) for different applications.

In one aspect the molecule has been shown to both simplify and shorten the assay development time for analyte detection assays while at the same time being amenable to a wide range of detection technologies.

Thus, in one example, described herein is the development of a molecule that simplifies and accelerates the development of analyte detection assays and analyte detection reagents, such as small molecule detection assays and small molecule detection analytes. In a specific example, the design and synthesis of the heterobifunctional linker is described, and we demonstrate the ability of the linker to covalently couple to multiple reagents, thereby creating reagents that can be easily conjugated to other substrates. Furthermore, we describe the design and synthesis of suitable gold nanoparticles (AuNPs) for conjugated analytes "decoration", and demonstrate the ability of the conjugated analytes to be coupled to the designed gold nanoparticles (AuNPs). The surface-conjugated analyte was used to prepare suitable antibodies via phage panning and demonstrate how metabolites can be detected using reagents binding proteins and the prepared reagents-linker-AuNPs using a lateral flow assay. The ability to prepare gold-labelled metabolites provides detection methods including absorbance, fluorescence, surface plasm on resonance, surface-enhanced Raman spectroscopy and electrical impedance.

In one example, there is described a method of manufacture of a water soluble heterobifunctional linker (L1), comprising:

a. producing tetraethylene glycol (TEG) p-toluene sulfonate (5) by tosylation of tetraethylene glycol with p-tosylchloride;

b. producing tetraethylene glycol azide (6) by nucleophilic substitution of tetraethylene glycol p-toluene sulfonate (5) with sodium azide in DMF;

c. producing p-toluene sulfonate tetraethylene glycol azide (7) by tosylation of tetraethylene glycol azide (6);

d. producing azide tetraethylene glycol thioacetate (8) by nucleophilic substitution of p-toluene sulfonate tetraethylene glycol azide (7) with potassium thioacetate.

e. producing TEG-"Clicked"-Alcohol (9) by reaction of azide tetraethylene glycol thioacetate (8) with 4-pentyn-1-ol to form 1,4-disubstitued-1,2,3-triazole;

f. producing the soluble heterobifunctional linker (L1) by removing excess copper from the TEG-"Clicked"-Alcohol (9) in step (e) and oxidizing by Swern oxidation.

In one example, there is provided a method of producing an AuNP-L1-analyte conjugate of Formula (I),

comprising, reacting a heterobifunctional linker (L1) with the free amine function of a label and conjugating AuNP to the thiol group of the L1, to form the AuNP-L1-analyte conjugate.

In one example, there is provided a method of producing an label-analyte conjugate of Formula (II),

comprising, reacting a heterobifunctional linker (L1) with the free amine function of an analyte and conjugating label to the thiol group of the L1, to form the label-L1-analyte conjugate.

In one example, there is described a water soluble heterobifunctional linker (L1) having the structure of Formula III:

wherein, A is a thiol group; B is a PEG linker moiety; C is an aldehyde group.

The term "polyethylene glycol" (PEG) refers to linear or branched oligomeric and polymeric polyether polyols.

In some examples PEG refers to native PEG as well as derivatives thereof.

In some examples PEG refers to ethylene glycol, diethylene glycol, triethylene glycol, tetraethylene glycol, pentaethylene glycol, hexaethylene glycol, and oligoethylene glycol and derivatives of these compounds. In some examples PEG refers to polymers and oligomers from ethylene oxide. In some examples PEG is represented by the structure $X-(CH_2CH_2O)_n-Y$. In some examples X includes but is not limited to OH and Y includes but is not limited to H, and n is larger than 0, preferably larger than 1, more preferably larger than 2. In a specific example, L1 is a compound of the following formula (IIIa)

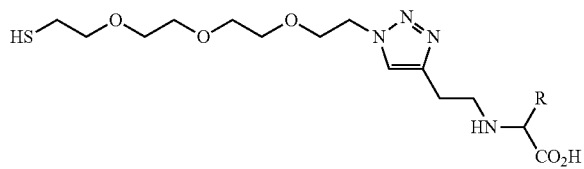

In a specific example, L1 is a compound of the following formula (IIIb)

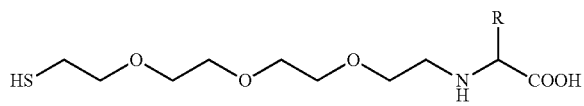

In some examples, the term "label," as used herein refers to a substance which is incorporated into a compound, such as L1, and is readily detected.

In some example, the label is a detectable label.

The term "detectable label," as used herein, refers to a label which is observable using analytical techniques including, but not limited to, fluorescence, chemiluminescence, electron-spin resonance, ultraviolet/visible absorbance spectroscopy, mass spectrometry, nuclear magnetic resonance, magnetic resonance, electrochemical and electrical methods, including but not limited to impedance measurements.

Thus, the term "label" includes, but is not limited to, a substance, such as a chemical moiety or protein which is incorporated into a compound and is readily detected. The label can be directly detectable (fluorophore) or indirectly detectable (hapten or enzyme). Such labels include, but are not limited to, radiolabels that can be measured with radiation-counting devices; pigments, dyes or other chromogens that can be visually observed or measured with a spectrophotometer; spin labels that can be measured with a spin label analyzer; and fluorescent labels (fluorophores), where the output signal is generated by the excitation of a suitable molecular adduct and that can be visualized by excitation with light that is absorbed by the dye or can be measured with standard fluorometers or imaging systems, for example. The label can be a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term label can also refer to a "tag" or hapten that can bind selectively to a conjugated molecule such that the conjugated molecule, when added subsequently along with a substrate, is used to generate a detectable signal. Numerous labels are known by those of skill in the art and include, but are not limited to, particles, fluorophores, haptens, enzymes and their colorimetric, fluorogenic and chemiluminescent substrates and other labels.

Specific examples of detectable labels include, but are not limited to, a chemiluminescent group, a chromophore, a dye, a fluorophore, a radiolabel, metals, metal nanoparticles, colloidal metal, nano particle colloidal metal, core-shell nanoparticles, such as nanoparticles comprising a dielectric coated with metal. Preferably the metal is selected from gold, silver, platinum and palladium. More preferably the metal is gold.

In some example, the label is biotin or tag peptides.

The term "chemiluminescent group," as used herein, refers to a group which emits light as a result of a chemical reaction without the addition of heat.

The term "chromophore," as used herein, refers to a molecule which absorbs light of visible wavelengths, UV wavelengths or IR wavelengths.

The term "dye," as used herein, refers to a soluble, coloring substance which contains a chromophore.

The term "fluorophore," as used herein refers to a composition that is inherently fluorescent or demonstrates a change in fluorescence upon binding to a biological compound or metal ion, i.e., fluorogenic. Fluorophores may contain substitutents that alter the solubility, spectral properties or physical properties of the fluorophore. Numerous fluorophores are known to those skilled in the art and include, but are not limited to coumarin, cyanine, benzofuran, a quinoline, a quinazolinone, an indole, a benzazole, a borapolyazaindacene and xanthenes including fluoroscein, rhodamine and rhodol as well as semiconductor nanocrystals and other fluorophores.

In some examples, the label is a radioactive nuclide (e.g., $^{125}I$, $^{3}H$, $^{14}C$, $^{32}P$).

In some example, the label is gold, for example, gold clusters, colloidal gold, or core shell particles, or core shell nanoparticles wherein the shell consists of gold.

The term "analyte" as used herein refers to a substance, compound or component. In some example, the analyte is a substance, compound, or component whose presence or absence in a sample is to be detected.

The term "analyte of interest", as used herein, means any molecule, or aggregate of molecules. Also included are fragments of any molecule found in a sample. An analyte of interest can be an organic compound, an organometallic compound, or an inorganic compound.

In some examples, the analyte includes, but is not limited to a metabolite, an amino acid, a herbicide, a pesticide, an environmental pollutant, an analyte, a veterinary drug, a drug, a drug of abuse, and/or a small molecule.

In other examples, the analyte includes, but is not limited to a nucleic acid (e.g., DNA, RNA), an antigen, a receptor, a receptor ligand, or a peptide, a lipoprotein, a glycoprotein, a ribo- or deoxyribonucleoprotein, a polysaccharide, a lipopolysaccharide, a lipid, a fatty acid, a vitamin, a pharmaceutical compound (e.g., tranquilizers, barbiturates, opiates, alcohols, tricyclic antidepressants, benzodiazepines, anti-virals, anti-fungals, steroids, cardiac glycosides, or a metabolite of any of the preceding), a hormone, a growth factor, an enzyme, a coenzyme, an apoenzyme, haptens, lechtins, a substrate, a cellular metabolite, a cellular component or organelle (e.g., a membrane, a cell wall, a ribosome, a chromosome, a mitochondria, or a cytoskeleton component). Also included are environmental pollutants.

The term "analog of the analyte of interest", as used herein, means a substance that competes with the analyte of interest for binding to a specific binding partner. An analog of the analyte of interest can be a known amount of the analyte of interest itself that is added to compete for binding to a specific binding partner with analyte of interest present in a sample.

The term "metabolite," as used herein, refers to a derivative of a compound which is formed when the compound is metabolized.

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound.

The term "amino acid" as used herein refers to a group or compound that consists of an amino group, a carboxyl group, an H atom and a distinctive R group (or side chain). "Amino acid" includes, α-amino acids, β-amino acids, δ-amino acids, and γ-amino acids. α-Amino acids consists of an amino group, a carboxyl group, a H atom and a distinctive R group which is bonded to the α-carbon atom. "Amino acid" includes natural amino acids, unnatural amino acids, amino acid analogs, amino acid mimics, and the like.

The term "natural" as used herein refers to a group or compound that is present in or produced by nature.

The term "unnatural" or "non-natural" refers to a group or compound that is not present in or produced by nature. An "unnatural" or "non-natural" group or compound is typically produced by human intervention. An "unnatural" or "non-natural" group or compound is artificial.

In one example, the term "amino acid" refers to one of the naturally occurring twenty amino acids (i.e. α-amino acids), as shown below. Amino acids consist of an amino group, a carboxyl group, an H atom and a distinctive R group (or side chain), all of which are bonded to an α-carbon atom. As a result of containing three differing groups on the α-carbon atom, amino acids contain a chiral center, and therefore may exist as either of two optically active enantiomers, the D- and the L-. Naturally occurring acids are found as their L-derivatives.

In another example, the amino acid is an "unnatural amino acid", "non-natural amino acid", "amino acid analog", "amino acid mimic". "Unnatural amino acid", "non-natural amino acid", "amino acid analog", "amino acid mimic" and the like, as used herein, refer to an amino acid that is not one of the 20 natural amino acids. These terms refer to amino acids wherein the fundamental amino acid molecule has been modified in some way. Such modifications include, though are not limited to side chain variations; substitutions on, or alterations to, the amino-CH-carboxyl backbone; D-enantiomers; combinations thereof and the like.

These terms also include, but are not limited to, amino acids which occur naturally but are not naturally incorporated into a growing polypeptide chain. Further, these terms also include, but are not limited to, amino acids which do not occur naturally and may be obtained synthetically or may be obtained by modification of natural, naturally occurring or non-natural amino acids.

In one example, the amino acid is glutamate, or histidine.

The term "small molecule", as used herein, refers to a chemical agent including, but not limited to a compound, a chemical compound, a composition, a pharmaceutical composition, nucleobases, nucleosides, polynucleotides, polynucleotide analogs, aptamers, nucleotides, nucleotide analogs, organic or inorganic compounds (i.e., including heteroorganic and organometallic compounds), and salts, esters, carbohydrates, and other pharmaceutically acceptable forms of such compounds.

The term "polypeptide" as used herein refers to a polymer of amino acids. The terms "protein" and "polypeptide" are used interchangeably herein. A peptide is a relatively short polypeptide, typically between about 2 and 60 amino acids in length.

Polypeptides typically contain amino acids such as the 20 L-amino acids that are most commonly found in proteins. However, other amino acids and/or amino acid analogs known in the art can be used.

One or more of the amino acids in a polypeptide may be modified, for example, by the addition of a chemical entity such as a carbohydrate group, a phosphate group, a fatty acid group, a linker for conjugation, functionalization, etc. A polypeptide that has a nonpolypeptide moiety covalently or noncovalently associated therewith is still considered a "polypeptide". Polypeptides may be purified from natural sources, produced using recombinant DNA technology, synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated.

The term "derivative" as used herein refers to peptides which have been chemically modified, for example by ubiquitination, labeling, pegylation (derivatization with polyethylene glycol) or addition of other molecules. A molecule is also a "derivative" of another molecule when it contains additional chemical moieties not normally a part of the molecule. Such moieties can improve the molecule's solubility, absorption, biological half-life, etc. The moieties can alternatively decrease the toxicity of the molecule, or eliminate or attenuate an undesirable side effect of the molecule, etc.

In one example, the polypeptide is carnosine.

In some example, the metabolite is a metabolite in Table 1.

Table 1 Examples of metabolites:

| Metabolite | Normal Concentration in Blood (µM) | Normal Concentration in Urine (µmol/mmol creatinine) |
|---|---|---|
| Asymmetric Dimethylarginine (ADMA) | 0.41-0.79 | 2.50-3.34 |
| Aldosterone | 0.000008-0.000044 | 0.006-0.014 |
| Aminoadipic acid | 0.0-5.0 | 3.4-11.2 |
| Beta-Hydroxybutyrate | 40-80 | 23.6-41.0 |
| Betaine | 20.0-144.0 | 6.4-92.7 |
| Billirubin | 5.0-21.0 | 0.0019-0.21 |
| Carnosine | 5.54-7.54 | 0.8-6.2 |
| Choline | 8.7-12.5 | 1.4-6.1 |
| Creatinine | 50.0-80.0 | 800-1100 |
| Estradiol | 0.0-0.00018 (male) | 0.00034-0.00084 (female) |
| Folate | 0.011-0.036 | 0.000013-0.0026 |
| Formate | 23.9-219.5 | 8.55-32.23 |
| Glucose | 4070-4810 | 11.98-39.62 |
| Glutamate | 44.0-76.0 | 3.3-18.4 |
| Glutamine | 581-709 | 9.0-33.0 |
| Glycerol | 34.0-52.0 | 0.12-0.73 |
| Homocysteine | 7.0-11.0 | 0.48-3.42 |
| HPHPA | (unknown) | 0.00-90.0 |
| Indoxylsulfate | 9.8-18.2 | 14.48-25.0 |
| Lactate | 600-2300 | 0.0-0.25 |
| Leucine | 127.0-187.0 | 1.5-4.5 |
| Neopterin | 0.0109-0.0191 | 0.13-0.29 |
| Phenylalanine | 56.0-74.0 | 2.63-6.37 |
| Pyruvate | 38.0-88.0 | 0.54-8.67 |
| Taurine | 102.0-222.0 | 21.1-105.0 |
| Testosterone | 0.009-0.03472 (male) 0.00052-0.00243 (female) | 0.88-1.26 (male) 0.0000-0.0002 (female) |
| TMAO | 17.4-58.2 | 0.00-151.0 |
| Tyrosine | 57.0-87.0 | 4.3-13.3 |
| Uric Acid | 242.0-362.0 | 119.0-294.0 |
| Vitamin D | 0.063-0.221 | 0 |

In some examples, there is described a method of selecting an antibody specific for a analyte, comprising: screening a library comprising antibodies for binding of an antibody within said library to a analyte-L1 conjugate.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. In one example, an immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain (VL) and variable heavy chain (VH) refer to these light and heavy chains respectively. The heavy-chain constant domains that correspond to the different classes of immunoglobulins are termed "alpha," "delta," "epsilon," "gamma" and "mu" respectively. The subunit structures and three-dimensional configurations of different classes of immunoglobulins are well known. In one example, the antibody is a monoclonal antibody. In another example, the antibodies are humanized, chimeric, human, or otherwise-human-suitable antibodies. "Antibodies" also includes any fragment or derivative of antibodies.

Antibody fragments include, but are not limited to Fab, F(ab')2, and Fv antibody fragments. The term "epitope" refers to an antigenic determinant on an antigen to which the paratope of an antibody binds. Epitopic determinants usually consist of chemically active surface groupings of molecules (e.g., amino acid or sugar residues) and usually have specific three dimensional structural characteristics as well as specific charge characteristics.

In one example, the antibody library is a library of single chain antibodies (scFv).

The term "specifically binds to" means that an antibody can bind preferably in a competitive binding assay to the binding partner.

A "human-suitable" antibody refers to any antibody, derivatized antibody, or antibody fragment that can be safely used in humans for, e.g. the therapeutic methods described herein. Human-suitable antibodies include all types of humanized, chimeric, or fully human antibodies, or any antibodies in which at least a portion of the antibodies is derived from humans or otherwise modified so as to avoid the immune response that is generally provoked when native non-human antibodies are used.

In some aspects there is provided a lateral flow device(s).

In one aspect, there is provided a diagnostic test(s) and/or device for detecting an analyte in a sample.

The devices, systems and methods described herein may be used for measuring analyte levels in a sample obtained from a subject.

In some examples, the diagnostic test is in the form of a lateral flow device (LFD). In some examples, the LFD is for use in point-of-care diagnostics.

A lateral flow assay device for the analysis of sample may comprise (i) a housing, and (ii) a flow path.

The term "sample" or "test sample" as used herein refers to a biological sample. Samples from biological sources (i.e. biological samples) usually comprise a plurality of analytes, such as metabolites.

Biological samples may be obtained from a subject.

The term "subject", may refer to an animal, and can include, for example, domesticated animals, such as cats, dogs, etc., livestock (e.g., cattle, horses, pigs, sheep, goats, etc.), laboratory animals (e.g., mouse, rabbit, rat, guinea pig, etc.), mammals, non-human mammals, primates, non-human primates, rodents, birds, reptiles, amphibians, fish, and any other animal. In a specific example, the subject is a human.

Biological samples from a subject include, but are not limited to bodily fluids.

As used herein the term "bodily fluid" refers to any fluid found in the body of which a sample can be taken for analysis. Non-limiting examples of bodily fluids include blood, plasma, serum, lymph, sudor, saliva, tears, sperm, vaginal fluid, feces, urine or cerebrospinal fluid.

Biological samples from a subject also includes samples derived, e.g., by biopsy, from cells, tissues or organs. This also encompasses samples comprising subcellular compartments or organelles, such as the mitochondria, Golgi network or peroxisomes. Biological samples also encompass gaseous samples, such as volatiles of an organism. Biological samples may be derived from a subject.

Techniques for obtaining different types of biological samples are well known in the art.

In some examples, the biological sample is a plant sample.

The term plant sample as used herein refers to a whole plant or a part of a plant. This term is seen to include, but is not limited to, a locus of a plant, a cell of a plant, a tissue of a plant, an explant, seeds of a plant, or portions of a seeds of a plant. This term further contemplates a plant in the form of a suspension culture or a tissue culture including, but not limited to, a culture of calli, protoplasts, embryos, organs, organelles, etc.

Biological samples may be pre-treated before use. Pre-treatment may include treatments required to release or separate the compounds or to remove excessive material or waste. Suitable techniques comprise centrifugation, extraction, fractioning, purification and/or enrichment of compounds. Moreover, other pre-treatments are carried out in order to provide the compounds in a form or concentration suitable for compound analysis. For example, if gas-chromatography coupled mass spectrometry is used in the method of the present invention, it will be required to derivatize the compounds prior to the said gas chromatography. Suitable and necessary pre-treatments depend on the means used for carrying out the method of the invention and are well known to the person skilled in the art.

The flow path of the LFD (e.g. a chromatographic strip), in some examples, is provided by a carrier, through which the test substance or body fluid can flow by capillary action. In one example, the carrier is a porous carrier, for example a nitrocellulose or nylon membrane. In other examples, sections or all of the carrier may be non-porous.

The flow path will typically have a reagent-detection zone comprising a detection zone where a visible signal reveals the presence (or absence) of the reagent of interest. The test substance can be introduced into the LFD and flows through to the detection zone.

In some examples, the sample, for example a bodily fluid, is allowed to permeate through the sheet, strip or other material from one side or end to another.

Reagent detection may be based on competitive or non-competitive (e.g., sandwich) assays.

In a specific example, reagent detection is based on a competitive assay.

In one example of a competitive assay, the detection zone contains regions of immobile analyte-protein and/or derivatives. These bind and immobilize any of the labelled binding partners not already bound by the analyte in the sample, producing, for example, a coloured line or stripe. In this case the amount of label bound in the detection zone (and so the intensity of the coloured stripe) will be inversely proportional to the amount of analyte in the sample.

In use, if the analyte is present in the sample, it will bind to the labelled binding partners. In some embodiments, the intensity of the colour may be directly proportional to the amount of analyte. Here the detection zone comprises permanently immobilised unlabelled specific binding analyte for the same analyte. The relative positioning of the labelled binding partner and detection zone being such that a body fluid sample applied to the device can pick up labelled binding partner and thereafter permeate into the detection zone. The amount of bound label can be detected as a visible signal in the detection zone.

In another competitive assay example, a labelled analyte or analyte analogue may alternatively be provided and this is detected using immobilized specific binding partner (e. g. immobilized protein specific for the analyte) in the detection zone.

In another competitive assay example, a labelled analyte or analyte analogue is provided along with a specific binding partner (e.g. a protein specific for the analyte). The resulting mixture is conveyed to the detection zone presenting immobilized binding partner of the analyte or analyte analogue. The higher the amount of analyte in the sample, the higher the amount of free labelled analyte which leaves the conjugate release zone to be detected in the detection zone.

The label in the LFD may be quantifiable by conventional means or as described herein.

In one example, there is described a system for detecting a analyte in a sample, comprising: a substrate comprising a reagent binding analyte, and an AuNP-L1-analyte conjugate, Methods of the invention are conveniently practiced by providing the compounds and/or compositions used in such method in the form of a kit. Such a kit preferably contains the composition. Such a kit preferably contains instructions for the use thereof.

To gain a better understanding of the invention described herein, the following examples are set forth. It should be understood that these example are for illustrative purposes only. Therefore, they should not limit the scope of this invention in any way.

EXAMPLES

Example 1

Results and Discussion
Design and Synthesis of Thiolated Linker.

Figure 2A:
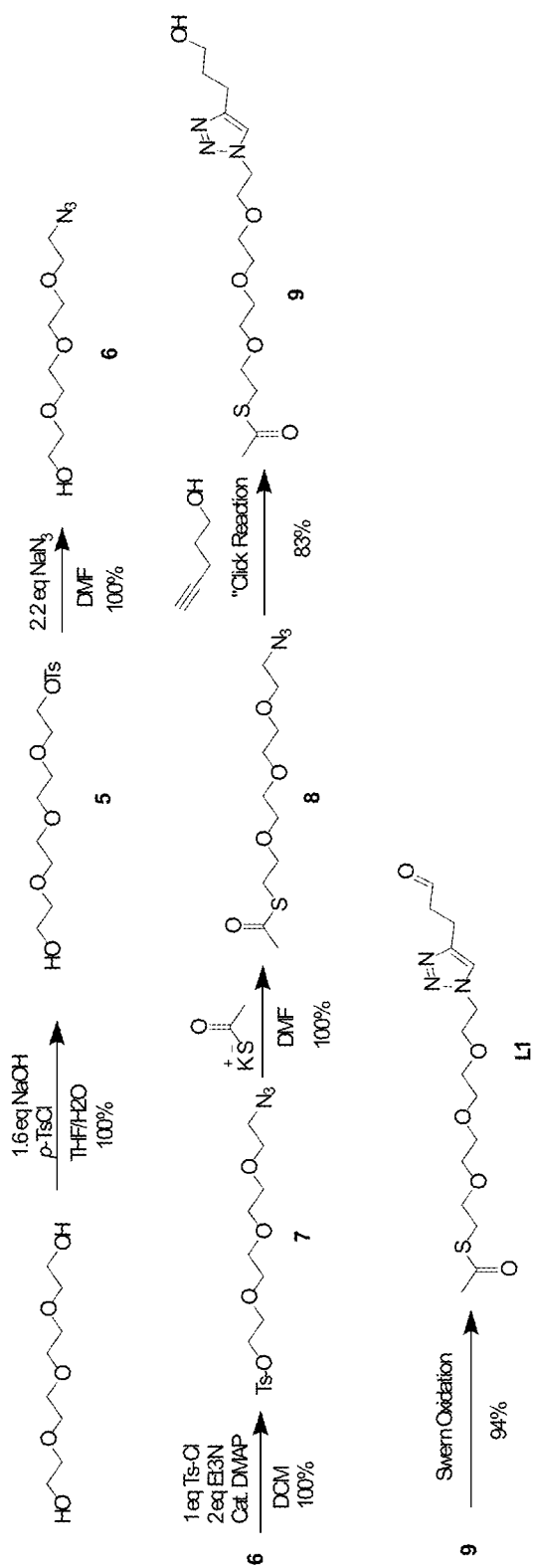
FIG. 2A depicts synthesis of linker-1 (L1) in 6 steps from tetraethylene glycol, yield a Linker L1, used for further conjugations.

We designed a heterobifunctional linker with an aldehyde group at one end, connected via a tetraethylene glycol linker to a thiol moiety at the other end (FIG. 1). The aldehyde can react very easily with primary amine group of aminoacids (for example) via reductive amination while the thiol function can conjugate to gold substrates such as AuNPs (or other thiol reactive substrates) via ligand exchange. The reagent, referred to herein as linker 1 (L1) was produced in six steps starting from tetraethylene glycol (FIG. 2 A-C). In the first step, tetraethylene glycol was tosylated using p-tosylchloride following standard procedures.[17] Second, to obtain compound 6, nucleophilic substitution of compound 5 with sodium azide in DMF was used to generate the azide6 in quantitative yield.[17] The thiolgroup was added through two more steps following tosylation of compound 6 to obtain compound 7 and nucleophilic substitution with potassium thioacetate to obtain compound 8 in quantitative yield. In the fifth step, the Cu(I)—catalyzed azide-alkyne Huigsen 1,3-dipolar cycloaddition (CuAAC) or so-called "click" reaction was implemented between an azidepolyethylenglycol and 4-pentyn-1-ol to form the 1,4-disubstitued-1,2,3-triazole[18-20] (FIG. 2). This reaction has been recognized as a very simple and effective chemistry for bioconjugation.[21] The triazole ring coupled with the PEG chain provides a very hydrophilic linker that contains a thiol moiety, which is known to form a strong covalent bond on almost any gold surface,[19,20] This reaction yields 9 as an alcohol that is filtered over silica gel to remove copper before being oxidized to an aldehyde via Swern oxidation to give the final compound L1 with 78% yield over the two final steps. The aldehyde functionality in L1 allows it to react with the free amines of aminoacids (as an example) through reductive amination.[22] Characterization of L1 was performed by NMR, IR and MS. Confirmation of L1 synthesis was demonstrated by Nuclear Magnetic Resonance (NMR) showing chemical shifts that confirm its structure by detection of either $H^1$ or $C^{13}$ nuclei (FIG. 3 (A)-(G)).

Metabolite Conjugation to L1:

To assess L1's ability to covalently couple to different metabolites in water, we generated 4 different L1 conjugates using glutamate, carnosine, histidine and leucine as target molecules. These metabolites were chosen because they all contained primary amines (which could react with the aldehyde) and they exhibited fundamentally different levels of water solubility and structure. Glutamate was reacted with L1 via reductive amination reaction in water using 1.1 equivalent of NaOH in the presence of magnesium sulfate and a slight excess 1.3 to 1.4 equivalents of the L1 aldehyde and then 1.2 equivalents of $NaBH_4$ to obtain compound 10 in 64% yield. The experimental set up included the addition of HCl to neutralize the reaction, whereupon the thioacetate was deprotected and the glutamate conjugate of L1 was obtained as a free thiol. Using the same procedure, the carnosine conjugate of L1 was synthesized yielding compound 11 as a free thiol with 62% yield. Reacting histidine with L1 gave compound 12 with 63% yield, and finally reacting leucine with L1 gave compound 13 with 69% yield. Overall, the yields of the pure L1-conjugates were between 60-70% with little dependence on the structure or water solubility of the target metabolite. More than a dozen other metabolite conjugates have been subsequently prepared using the L1 linker and similar yields have been consistently seen, including isoleucine and valine (manuscript in preparation). All metabolite-L1-conjugates exhibited the expected $^1H$ and $^{13}C$ NMR spectra of both the L1 linker and the corresponding metabolite (see supplemental materials). All the modified metabolites were found to possess excellent stability (up to two weeks with no evidence of degradation by NMR stored at 2-8 under Nitrogen to prevent dimerization) and solubility (up to 10 mg/mL) in aqueous solution. These properties gave us confidence that the L1-linker and the L1-metabolite conjugates could be used in metabolite sensing assays.[23-25]

Gold Nanoparticle Stabilization:

With several L1-metabolite conjugates in hand, the next step was to assess whether they could be attached to various substrates, including gold nanoparticles (AuNPs). However, in order to bind the L1-metabolite conjugates to gold, water-soluble, stable gold colloids had to be created. Citrate and cetyltrimethylammonium bromide (CTAB) are most commonly employed reagents used to stabilize AuNPs.[26] Unfortunately, CTAB has been shown to be toxic, and citrate AuNPs aggregate easily during thiolate modification or upon exposure to strong pH and salt conditions.[18,26] A number of other gold surface modification reagents have recently been developed, including PEG-triazole,[26] glutathione,[27] and mercapto-alkanes.[28] These linkers can stabilize AuNPs, but can only be produced in small quantities using rather undesirable organic solvents.[26,27] Although reduction reactions can be utilized for various thiol modified compounds, this route was deemed to be too tedious and inefficient for our purposes. As a result we chose to develop a new approach to create highly stable and very water-soluble citrate stabilized AuNPs.

We initially chose the Turkevich method to form gold citrate nanoparticles through citrate reduction.[29] Gold citrate nanoparticles are known to be very stable, consisting of a negatively charged shell that electrostatically stabilizes the positive gold surface. However, forming a covalent bond between a negative thiol and the gold surface is quite challenging as this negative driving force can cause aggregation. To avoid this, neutral pH addition reactions are typically used to link gold citrate nanoparticles with other molecules.[30]

With the citrate-stabilized AuNPs in hand, all four L1-modified metabolites were conjugated to the AuNPs through their thiol moieties to see if stable metabolite-conjugated AuNPs could be generated. Almost all of the initial attempts ended in failure, particularly for the histidine, leucine and carnitine conjugated citrate-AuNPs. Conjugation of these metabolites to the citrate AuNPs quickly led to aggregation and the formation of a black precipitate after just a few minutes of stirring. A number of attempts were made to solubilize the histidine, leucine and carnitine AuNPs. These included adjusting the solution pH below 2 and above 9 to see if the protonated and non-protonated modified metabolites will affect the stability or solubility of the AuNP. At an acidic pH (pH≤2) an AuNP conjugate formed, but the stability was poor, with the relatively quick formation of a black precipitate during centrifugation, which was not water soluble. At a more basic pH (pH≥9) no thiol reaction took place. The UV-Vis spectra showed no change with respect to characteristic citrate AuNP absorbance that could suggest any reaction. Additional pH values were tested, however, a stable gold colloid could not be generated that would last for more than 2-3 hours.

Figure 4:
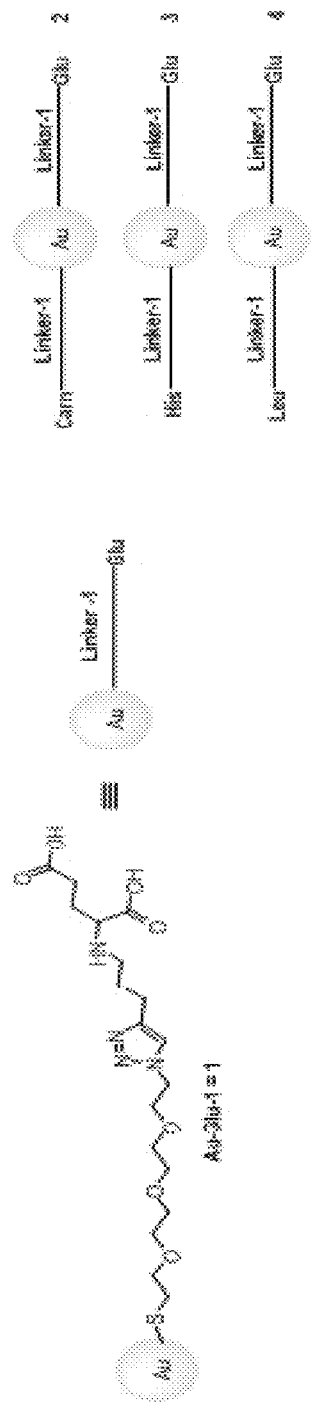
FIG. 4 is a general scheme for conjugated AuNPs. Gold citrate nanoparticles are modified with glutamate L1, before a second addition is done with carnosine, histidine, and leucine L1.

FIG. 4 is a general scheme for conjugated AuNPs. Gold citrate nanoparticles are modified with glutamate L1, before a second addition is done with carnosine, histidine, and leucine L1.

Figure 5:
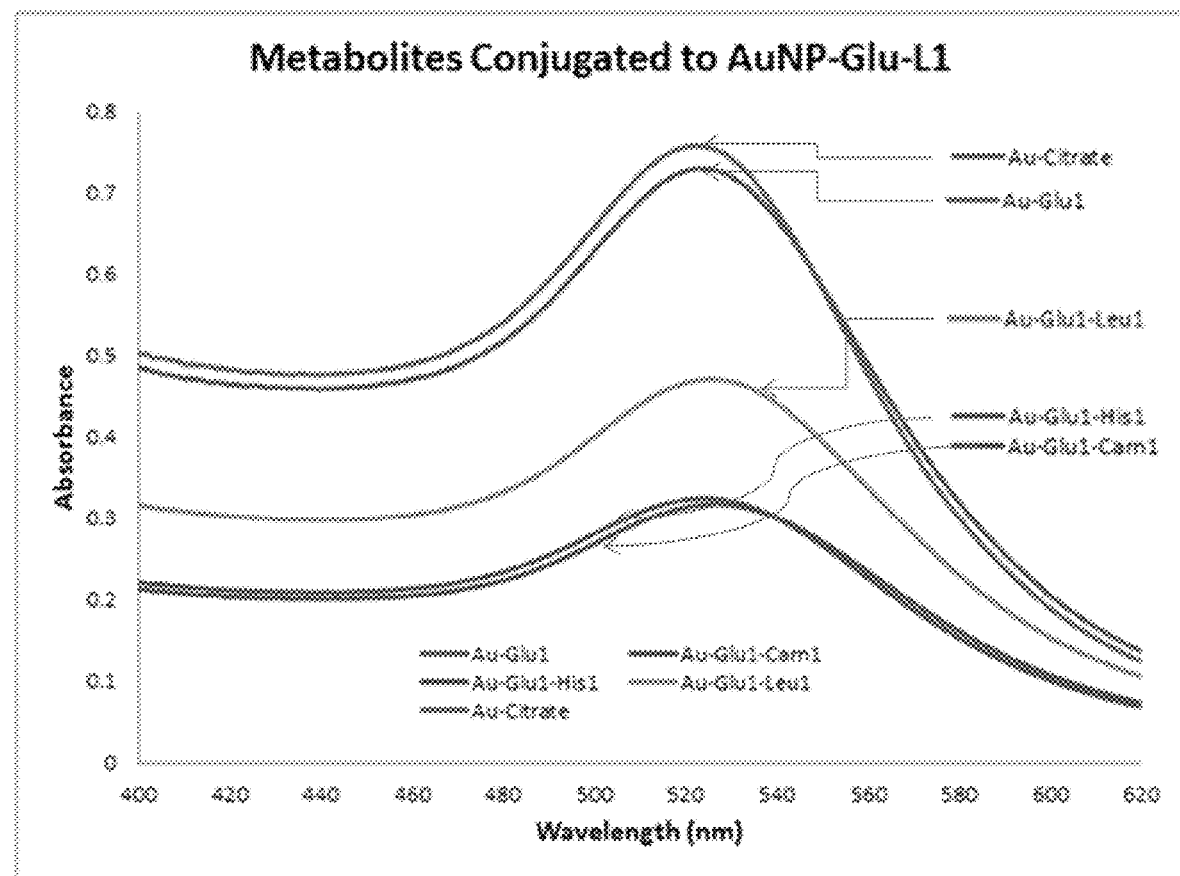
FIG. 5 is a UV-Vis spectra of functionalized AuNPs. UV spectra were obtained after AuNP conjugation.
Figure 6A:
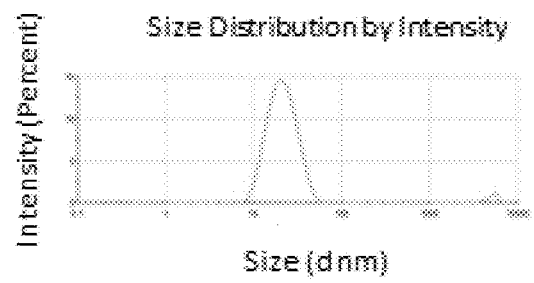
FIG. 6A-K depicts DLS—FIG. 6A Au-citrate FIG. 6B 1 (Au-Glu-1) FIG. 6C 2 (Au-Glu-2) FIG. 6D 4 (Carn-1-Au-Glu-1) FIG. 6E 6 (Carn-2-Au-Glu-1) FIG. 6F 8 (Carn-1-Au-Glu-2) FIG. 6G 10 (Carn-2-Au-Glu-2) FIG. 6H 3 (His-1-Au-Glu-1) FIG. 6I 5(His-2-Au-Glu-1) FIG. 6J 7 (His-1-Au-Glu-2 FIG. 6K 9 (His-2Au-Glu-2).
Figure 6B:
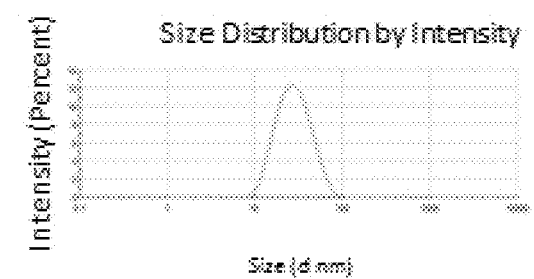
Figure 6C:
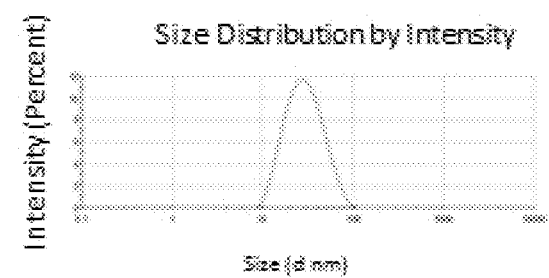
Figure 6D:
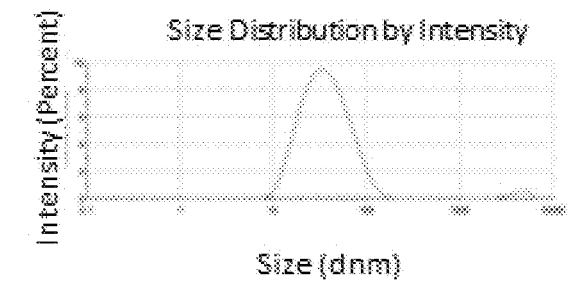
Figure 6E:
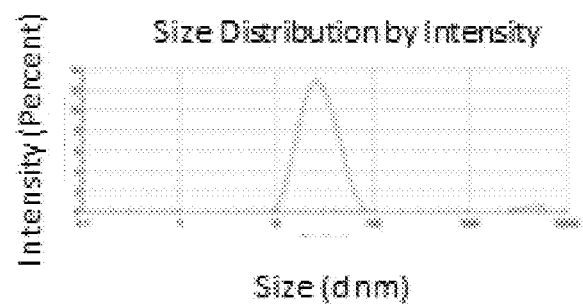
Figure 6F:
Figure 6G:
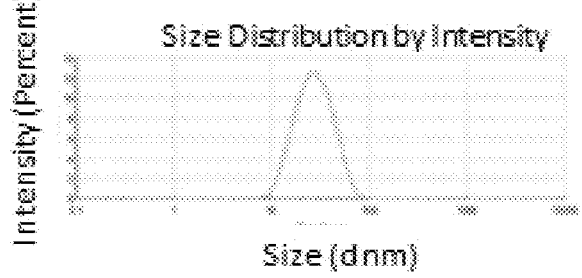
Figure 6H:
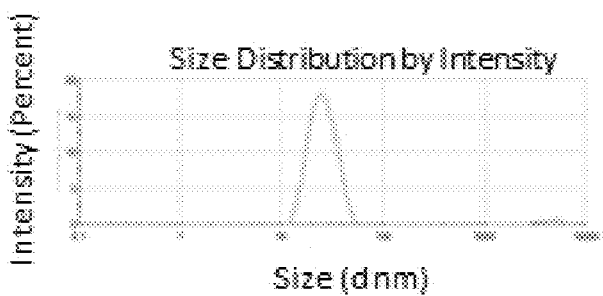
Figure 6I:
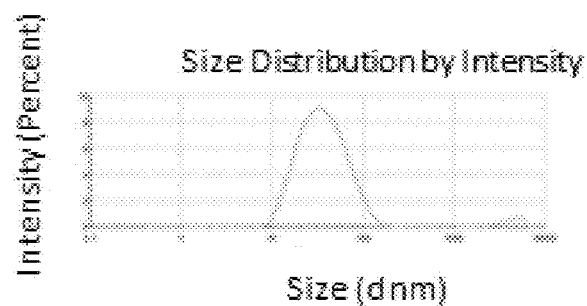
Figure 6J:
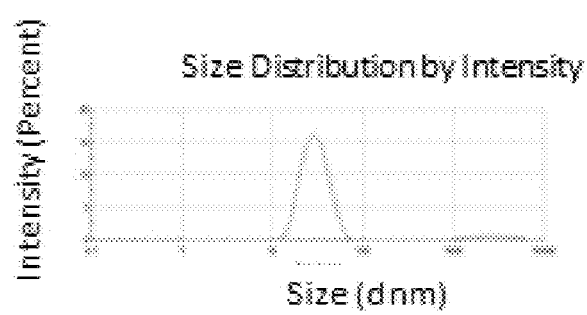
Figure 6K:
Figure 7A:
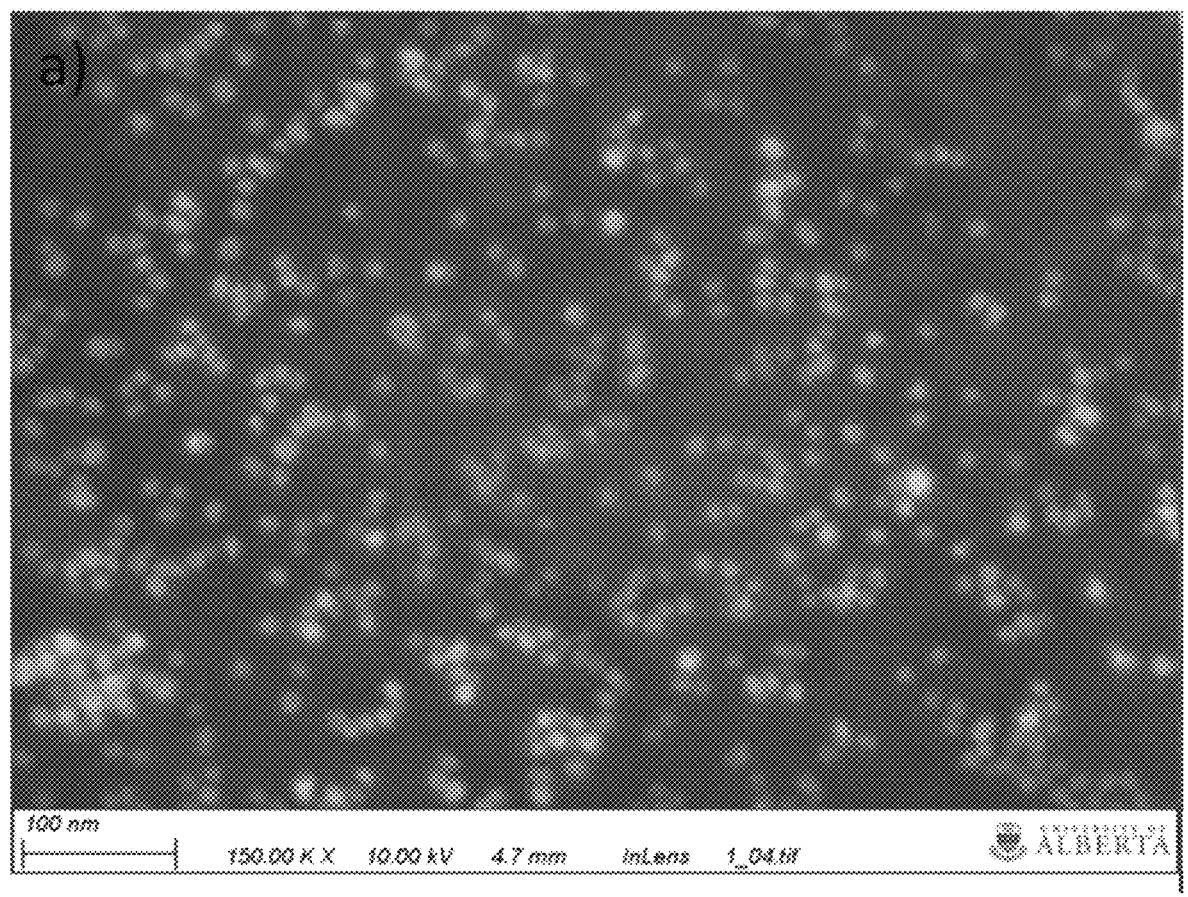
FIG. 7A-K depicts SEM images of conjugated AuNP.
Figure 7B:
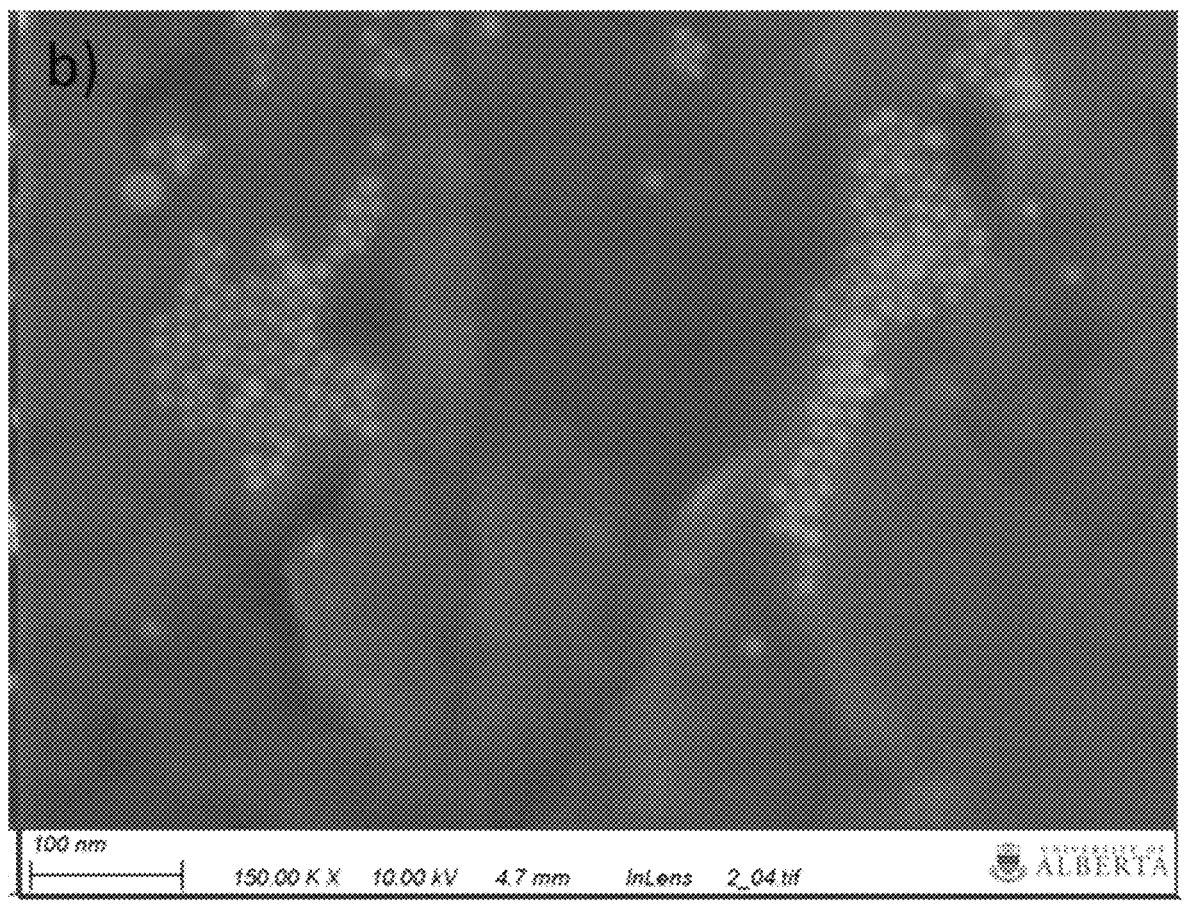
Figure 7C:
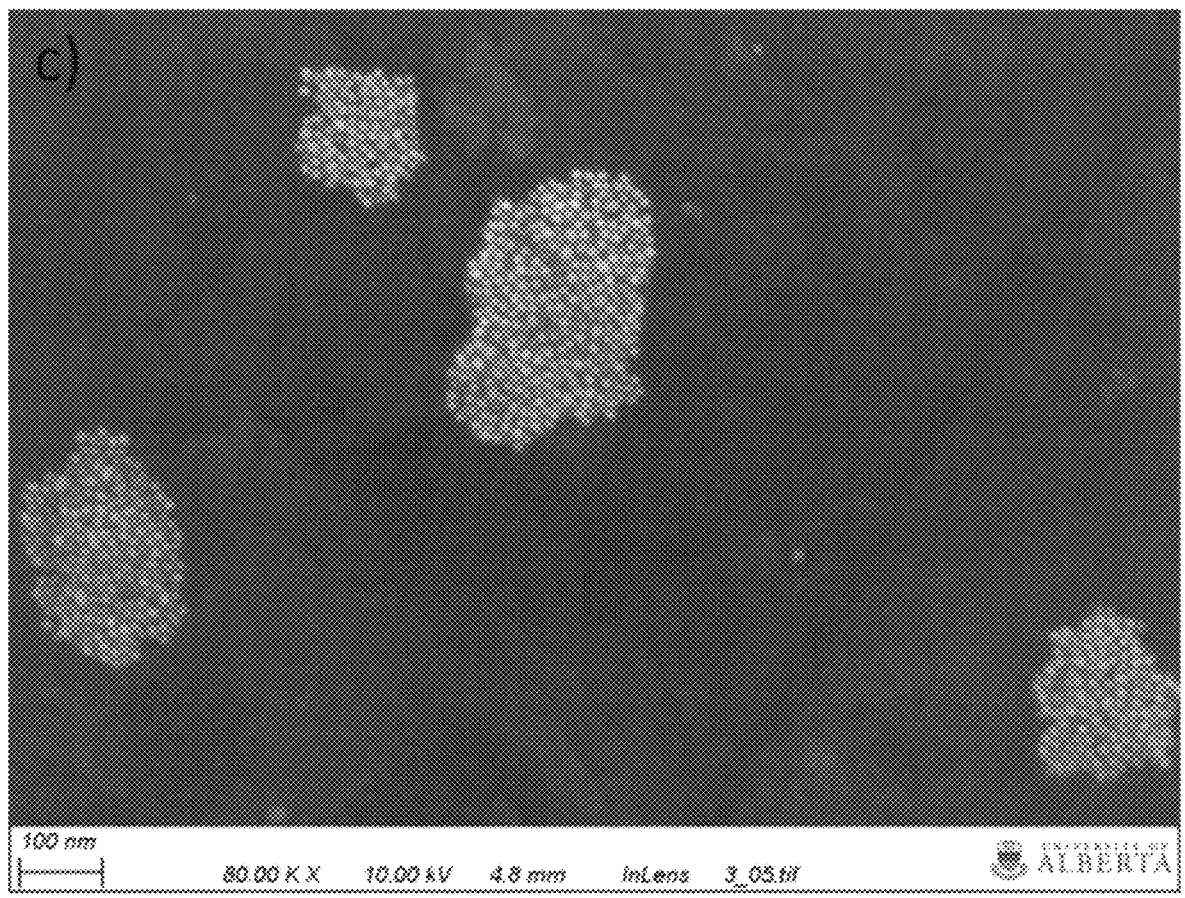
Figure 7D:
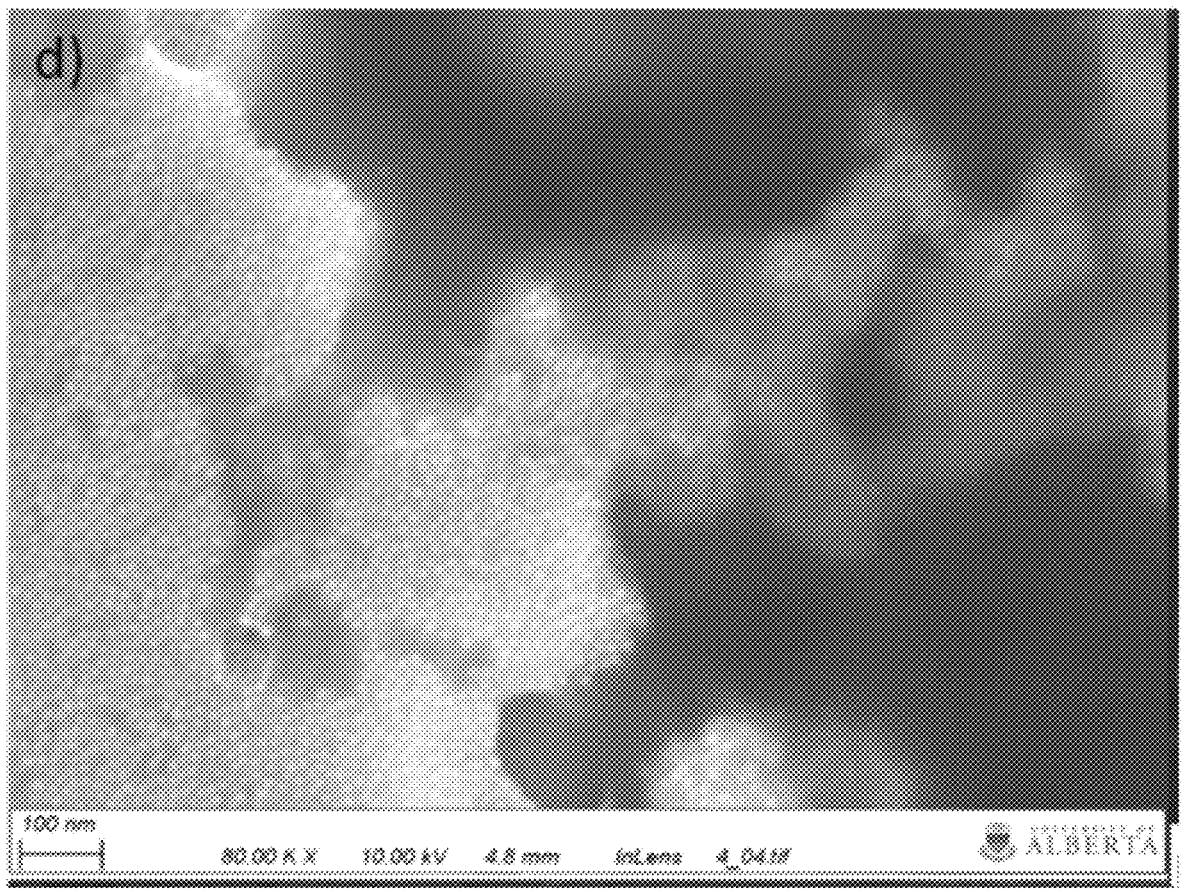
Figure 7E:
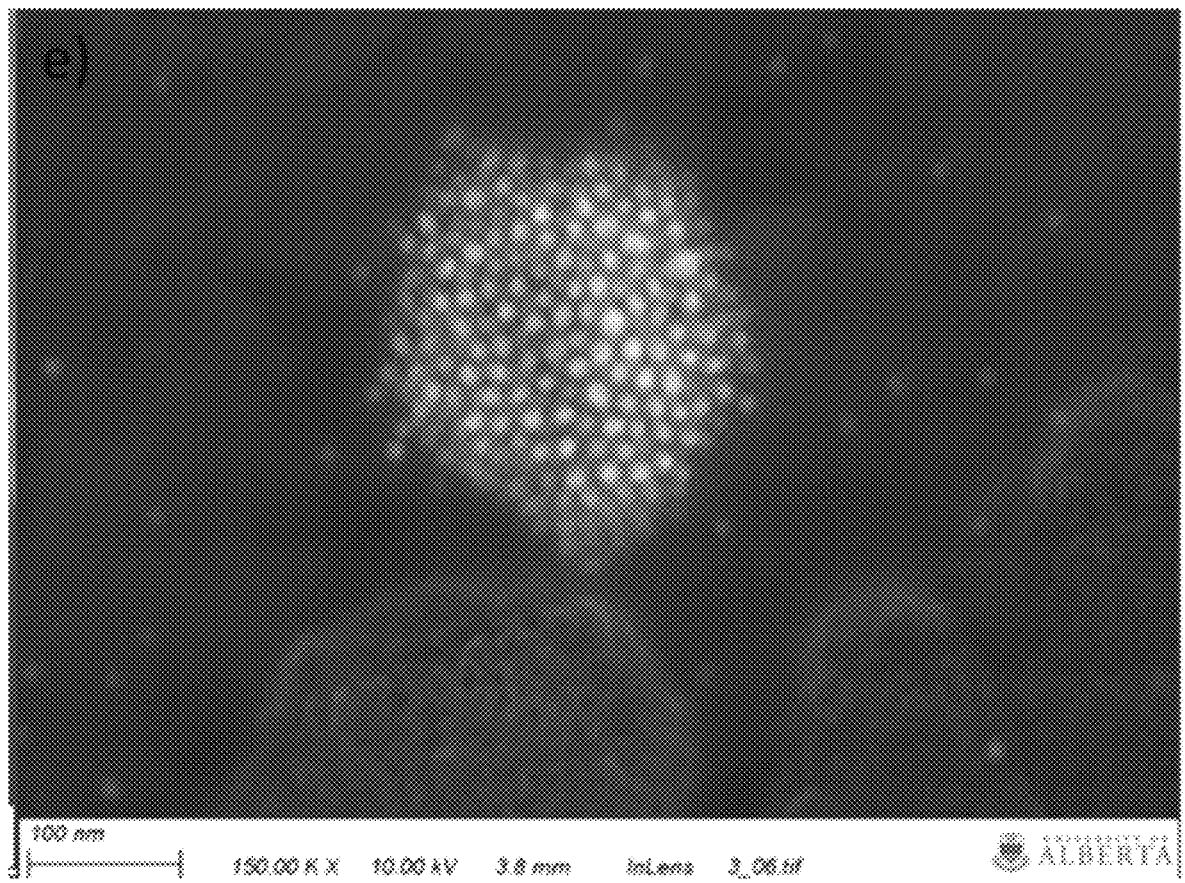
Figure 7F:
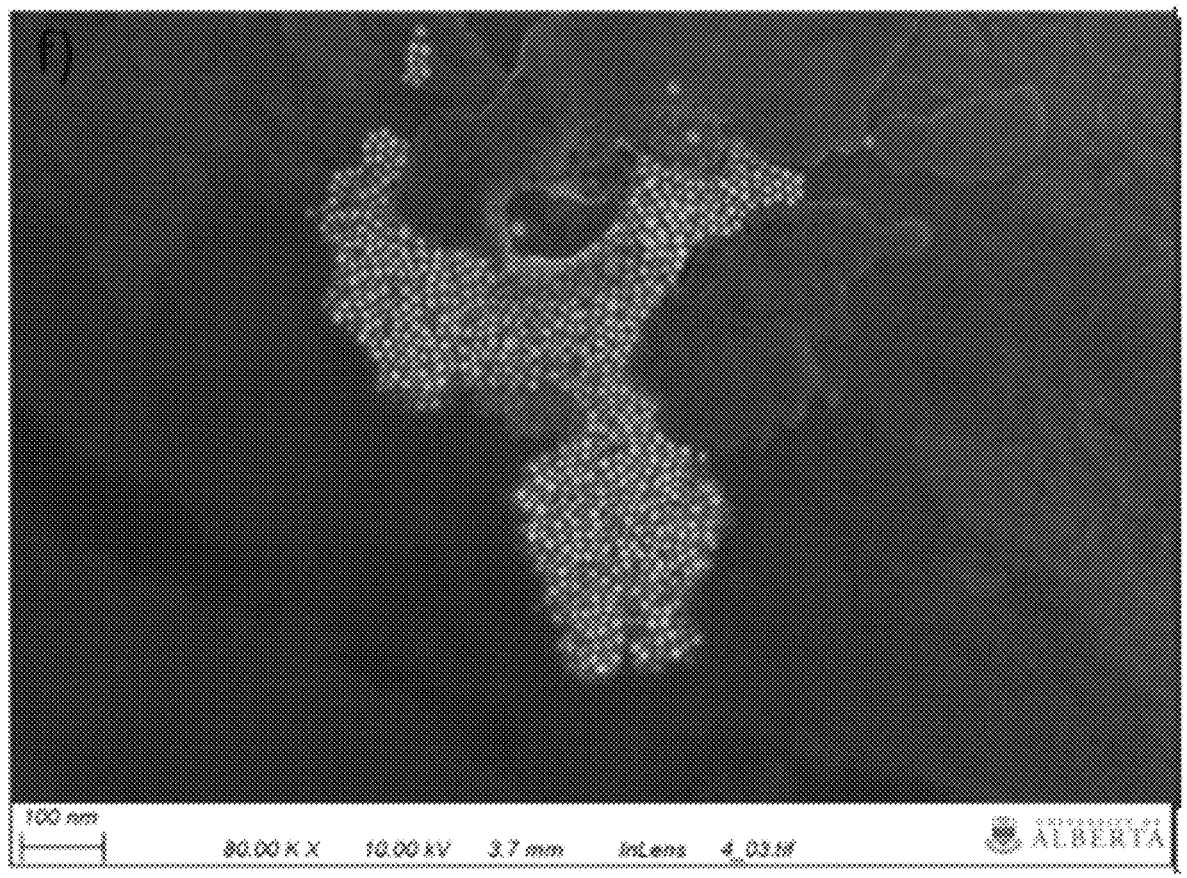
Figure 7G:
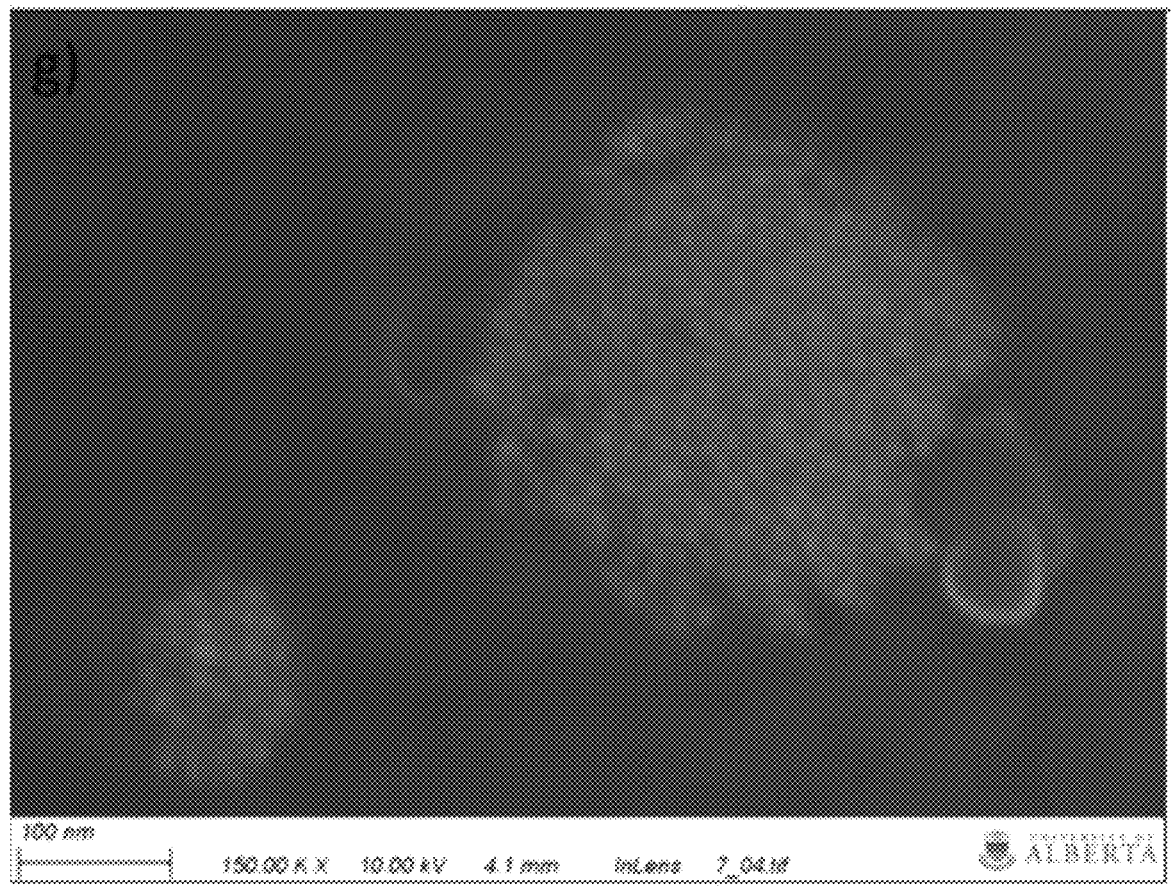
Figure 7H:
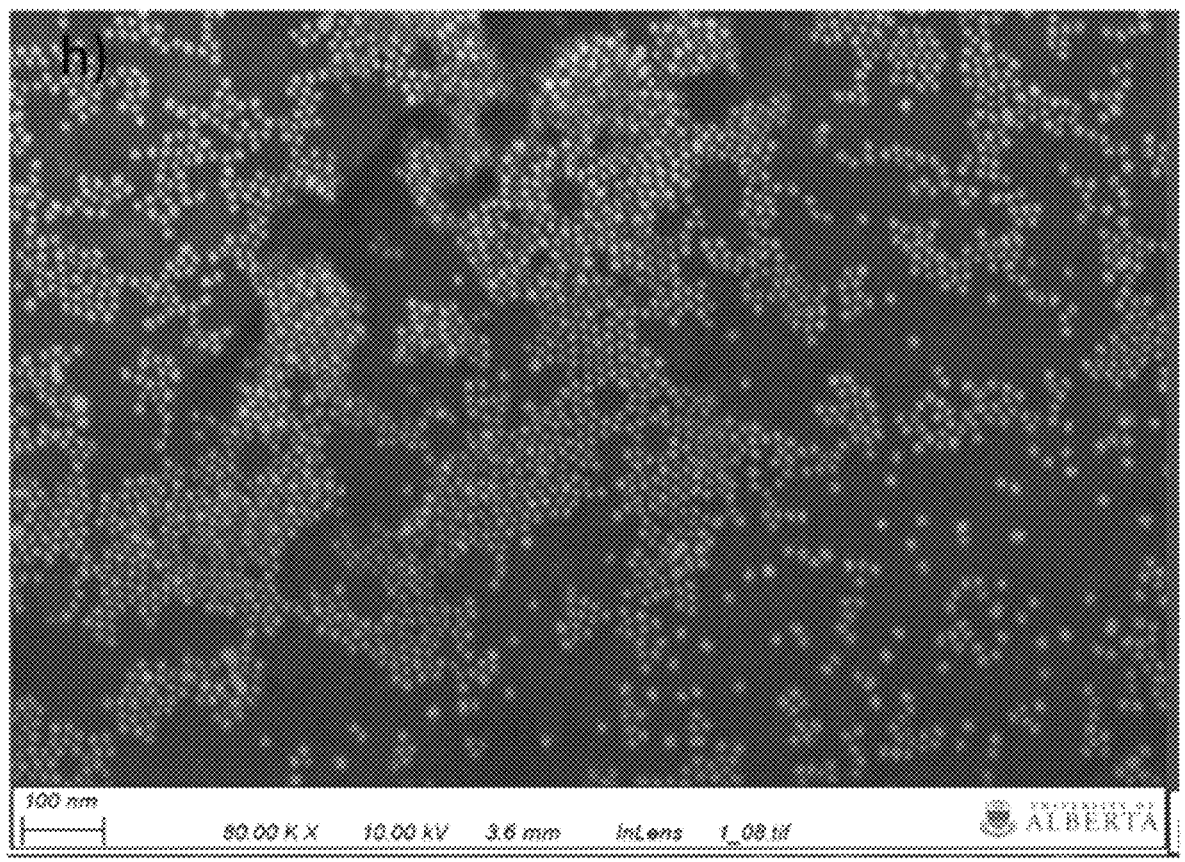
Figure 7I:
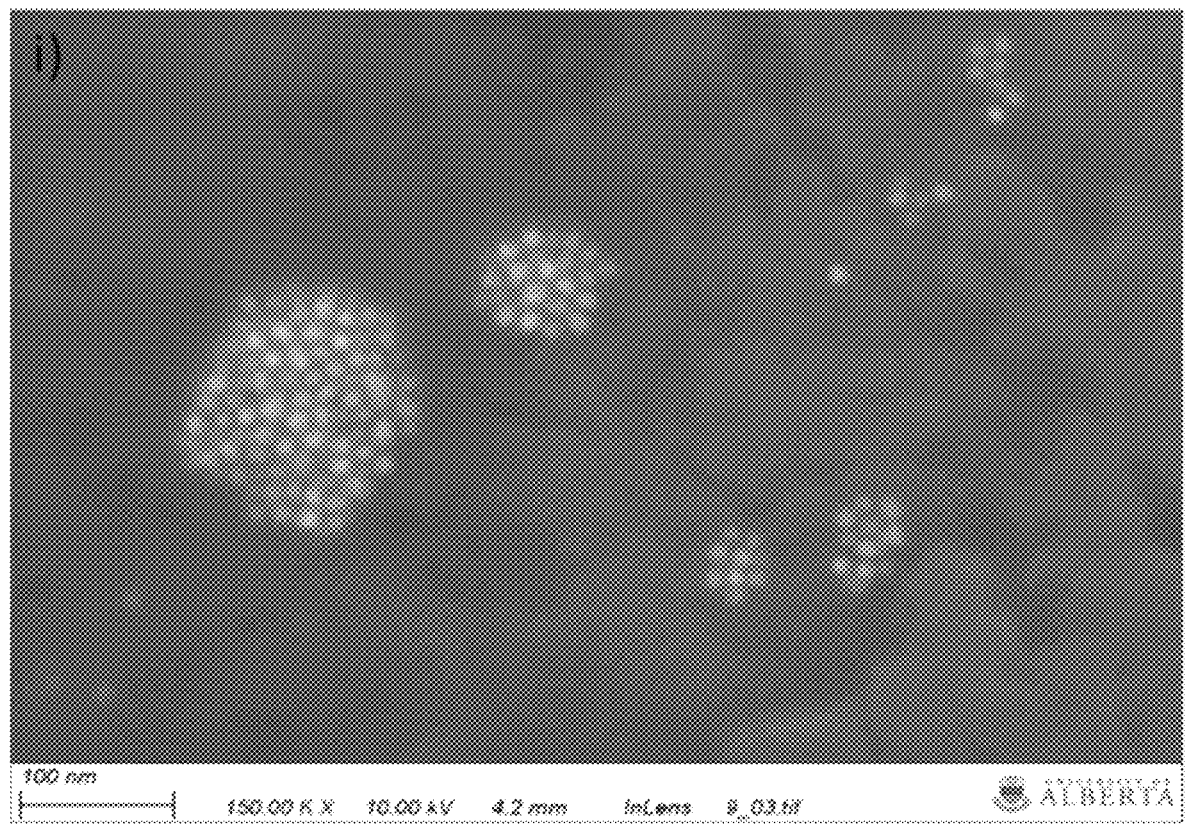
Figure 7J:
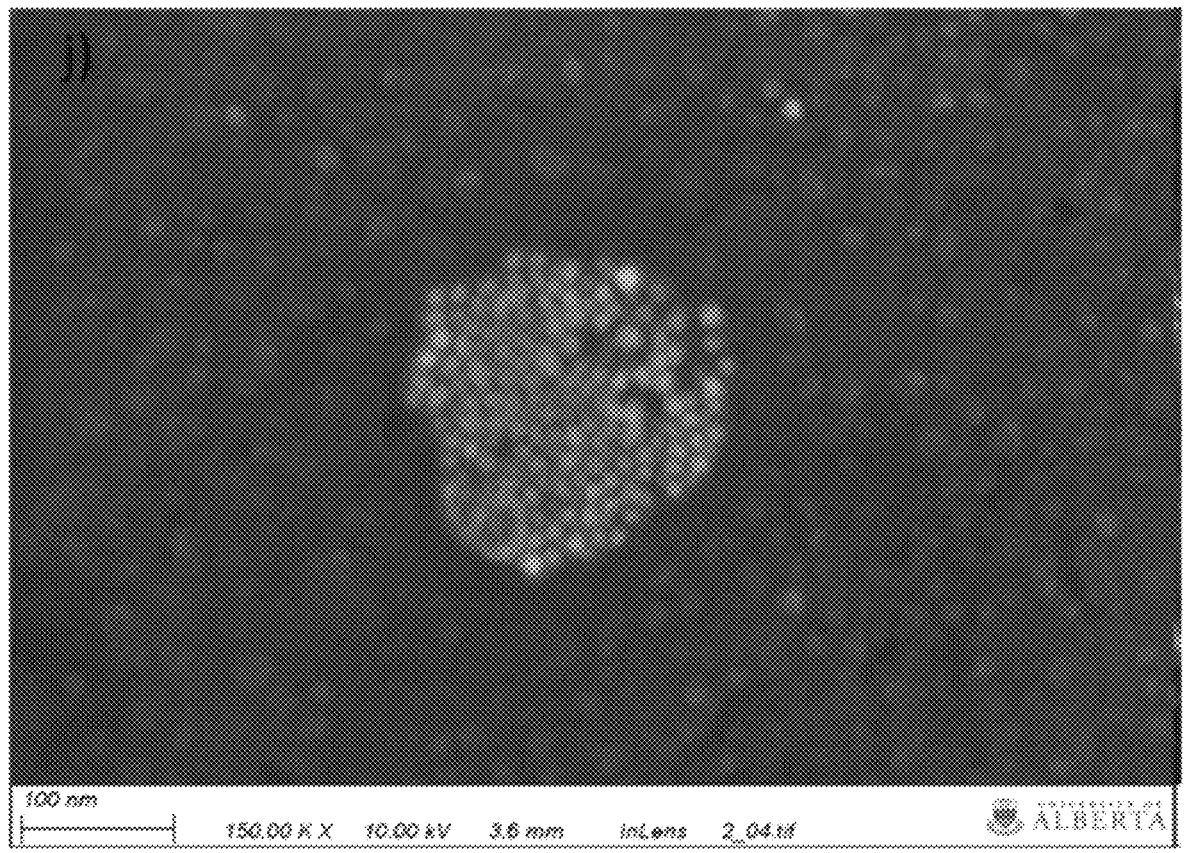
Figure 7K:
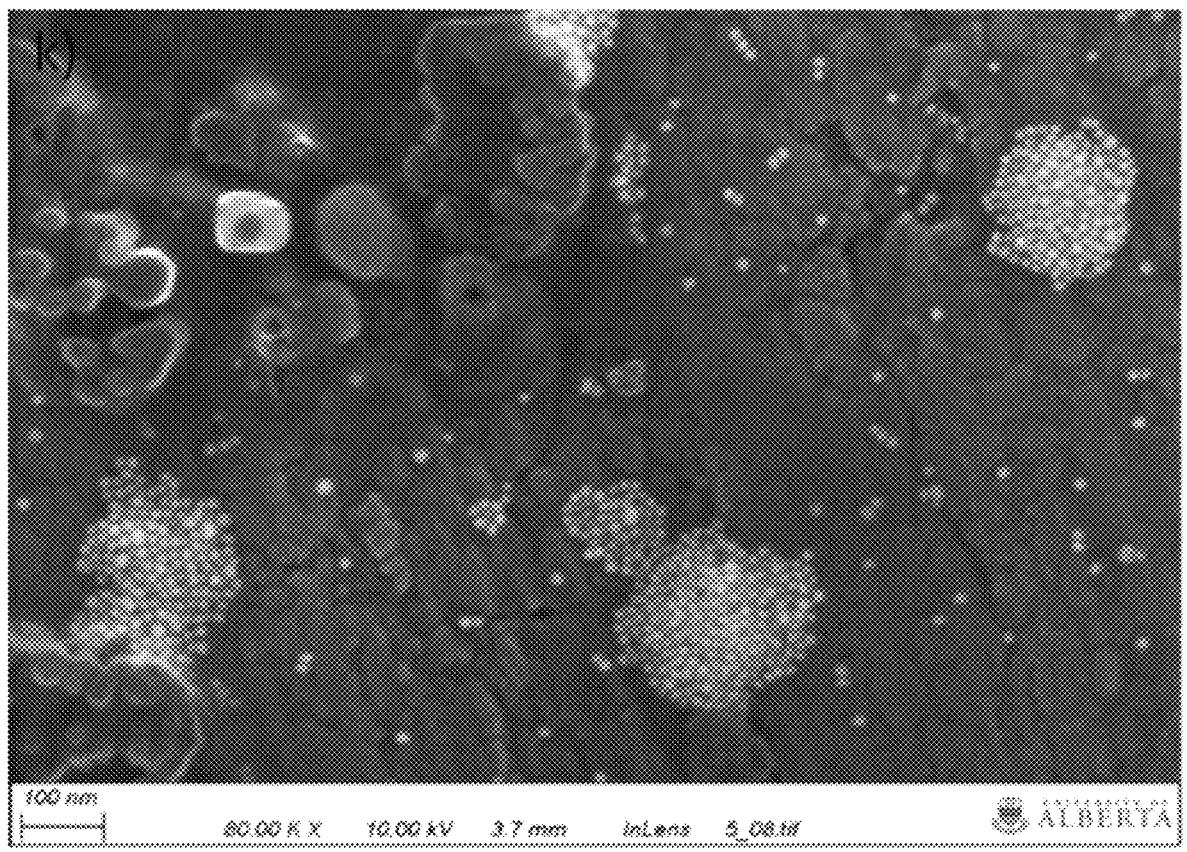

Surprisingly, only L1-modified glutamate-AuNP yielded a water-stable nanoparticle. To establish a baseline of what an ideal L1-modified metabolite AuNP should look like, the glutamate-L1-AuNP conjugate was examined in more detail using ultraviolet-visible spectroscopy (UV-Vis), dynamic light scattering(DLS) and scanning electron microscopy (SEM). The UV-Vis spectra (FIG. 5) of the gold citrate nanoparticles show an absorbance maximum at 522 nm, which matches with the expected 15-20 nm diameter of the AuNPs.31 The DLS spectrum (FIG. 6) confirmed the particle size, showing the average hydrodynamic diameter to be 22.5 nm, with the majority of AuNPs having diameters between 10-30 nm in solution. While the particles may not be perfectly uniform in size, they are very well dispersed. This is seen in the SEM of the AuNP conjugates (FIG. 7 (A)-(K)). The UV spectrum of the glutamate-L1-AuNP conjugate, exhibited a slight shift in the absorbance maximum to 523 nm, compared to 522 nm for the AuNP-citrate. In addition a slight drop in absorbance intensity was observed (FIG. 5). The red shift is seen as evidence that modification of the gold surface has taken place, as the particle size has increased due to the addition of the L1-glutamate conjugates to the gold surface. The drop in absorbance is due to the subsequent washings that are done to remove unwanted organic material and salts after surface modification, which decreased the concentration of the solution.

The fact that the L1-modified glutamate-AuNP was so stable on its own, suggested that it could serve as the stabilized AuNP to which other L1-metabolite conjugates could be added. In other words, using the water-stable Glutamate-L1-AuNP conjugate instead of the citrate-AuNPs as the nanoparticle substrate, would be more productive.

Preparation of Gold Nanoparticle Metabolite Conjugates:

From a stock solution of Glutamate-L1-AuNP conjugate (Glu-AuNP) 4 different colloidal suspensions were prepared by adding each of the 4 metabolite conjugates (L1-glutamate, L1-histidine, L1-carnosine, L1-leucine) to the Glu-AuNP solution. Stable versions of each of these metabolite-L1-GNP conjugates (also referred to as double conjugated AuNPs) were successfully made. Each was then assessed for long-term stability and water solubility and each was fully characterized using UV-Vis, DLS and SEM. In the stability/solubility tests of these double conjugated AuNPs, no noticeable aggregation took place even after prolonged (>10 hours) stirring. Water solubility tests showed that these double conjugated AuNPs have water solubility above 5 mg/mL. This was in marked contrast to the AuNPs prepared using citrate-AuNPs as the substrate, where precipitation was almost immediate. After their preparation, all the double conjugated samples were placed in the refrigerator and monitored for several months. Periodic checks indicated that these colloids exhibited remarkable stability with only modest levels of aggregation of these double conjugated AuNPs being initially detected after 2 months.

The characterization of all double conjugated AuNPs by UV-Vis spectroscopy is presented in Table 2.

TABLE 2

Wavelength values for the functionalized AuNPs. After conjugation, UV spectra were obtained and Maximum values shifts analyzed to confirm reaction had taken place.

| Compound | Wavelength (nm) |
|---|---|
| Au-Citrate | 522 |
| 1 Au-Glu-L1 | 523 |
| 2 Au-Glu-L1-Carn-L1 | 526 |
| 3 Au-Glu-L1-His-L1 | 525 |
| 4 Au-Glu-L1-Leu-L1 | 525 |

When conjugation is performed with L1-His to the Glu-AuNP substrate, the UV-Vis spectrum shows a slight red shift in wavelength for the product 3 (Glu-AuNP-His) with an absorbance maximum of 525 nm compared with 523 nm for 1(Glu-AuNP). This red shift suggests that the double-conjugation process is leading to an even larger nanoparticle or at least a particle with a larger average diameter than either Glu-AuNP or citrate-AuNP. When conjugation is performed with L1-carnitine (12) to the Glu-AuNP substrate (1) the resulting product 2 (Glu-AuNP-Carn) exhibits a slight red shift in its absorbance maximum. As we can see in Table 2, an absorbance at 526 nm is seen for 2 (compared to 523 for 1). The same shift was also observed for the L1-Leu conjugate and its product (Glu-AuNP-Leu).

When looking at the DLS data (FIG. 6A-K) we see that compared to the AuNP-citrate particles (with an average diameter of 22.5 nm), the Glu-AuNP particles have a diameter of 30.7 nm. This increase in the hydrodynamic diameter is due to the addition of longer PEG-metabolite moieties on the GNPs as well as through the increased stability of the particles (which means they are not transiently breaking apart, which would lead to a smaller average hydrodynamic diameter). This high stability and tight packing can be seen in the SEM images (FIG. 7A-K). This tight packing is thought to be due to a phenomenon called inter-nanoparticle bridging[32] and is only possible with highly polar organic groups being prevalent on the gold surface and in solution. This rationale also allows us to deduce the successful modification of our AuNPs.[32] The fact that we managed to not only stabilize our gold nanoparticles with a linker modified glutamate, but managed to add different metabolites on the surface suggests that it may be possible to prepare multiple metabolites on a single particle. This could open the door to preparing polyfunctional reagents for multiplexed testing and detection.

Figure 8A:
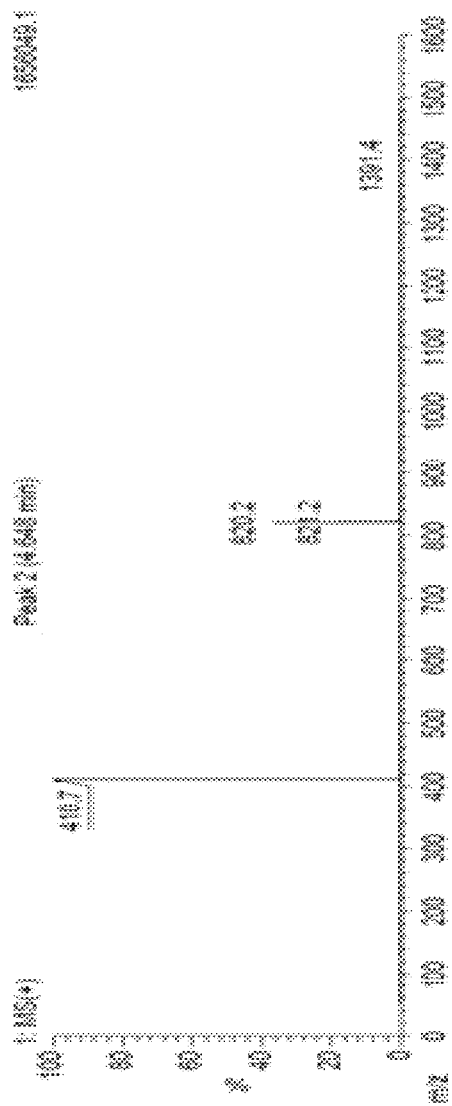
FIG. 8A-B Synthesis of 5-IAF conjugated metabolites.
Figure 8B:
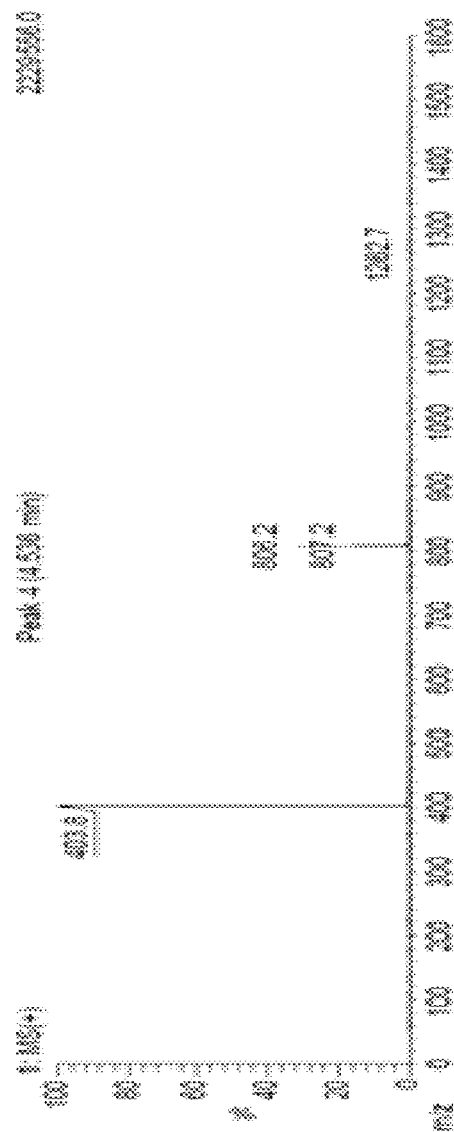

Generation of Fluorescein-Conjugated Metabolites:

We aimed to generate metabolites that would be suitable for assays that involve fluorescence readout instead of ANP detection. To this end, we used L1-conjugated metabolites and labeled them with Iodoacetamidofluorescein (5-IAF) through the thiol terminus of L1. Isoleucine, Valine or Glutamate conjugated to L1 were labeled with 5-IAF, which is a known thiol-reactive probe that is widely used to label bioconjugates with a fluorescein isomer.[33] Labeled L1-metabolites were analyzed by Mass Spectrometry after HPLC purification and peaks with expected molecular weights were observed confirming the synthesis of Ile-L1-IAF; Glu-L1-IAF and Val-L1-IAF (FIG. 8 (A)-(B)). Our results show that L1 confers the capability of conjugating metabolites to several types of labels, not just AuNPs.

Use of L1-Carnitine for Antibody Selection.

In addition to proving that L1-conjugated metabolites could be used to prepare stable, water-soluble, decorated AuNPs we also wanted to see if L1-conjugated metabolites could be used to prepare metabolite-specific antibodies. Specifically we chose L1-conjugated carnosine (as an example) to determine if this reagent could be used to create a metabolite-specific scFv for carnosine. L1-carnosine was first immobilized on maleimide-coated multiwall strips. This was achieved by generating a thioether bond between maleimide and the terminal thiol in the linker. A total of three different phage libraries expressing human single-chain antibodies were incubated in parallel with these carnosine-coated strips ($10^{12}$ cfu of phage). After 3 rounds of selection, individual clones (each encoding an anti body-phage fusion) were identified and grown separately on 96-well plates to carry out ELISA tests for their affinity against L1-carnosine.

Figure 9:
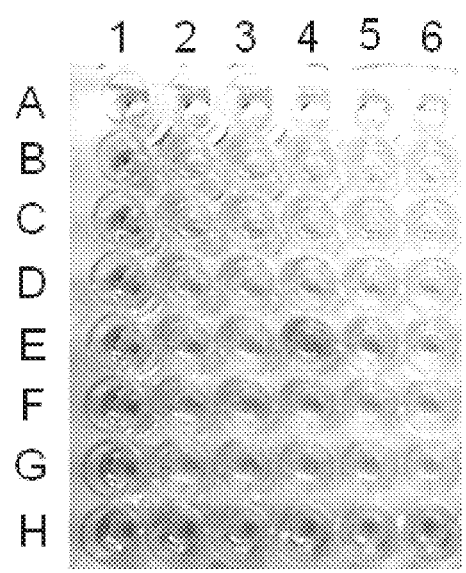
FIG. 9 depicts Monoclonal Phage ELISA. Phages selected against Carnosine were used to detect binding against Carnosine-L1 on ELISA plates. Wells A2, A4 and A6 are negative controls; wells H2, H4 and H6 are positive control (Ubiquitin). All other wells are clones obtained through Phage Display.

Duplicate plates were loaded with individual phage-antibody clones on each well. One plate was coated with BSA (nonspecific control) and the other plate was coated with carnosine-L1 and then blocked with BSA (Test plate). Our results show that several clones from each library exhibited signals well above the positive controls, indicating strong candidates for carnosine binding. In particular, clones E4 and F3 showed especially strong signals (FIG. 9). After appropriate subtraction of the BSA plate and Test plate absorbances, we found that F3 exhibited comparable levels with the positive control but E4 showed a significantly higher value (Table 3).

TABLE 3

Monoclonal Phage ELISA. Net Absorbance values (Carnosine ELISA minus BSA Elisa values) from clones as FIG. 9. Wells A2, A4 and A6 are negative controls; wells H2, H4 and H6 are positive control (Ubiquitin). All other wells are clones obtained through Phage Display. Libraries: Domain Antibody (Dab), Tomlinson I and J.

| | Library: | | | | | |
|---|---|---|---|---|---|---|
| | DAb | | Toml. I | | Toml. J | |
| | 1 | 2 | 3 | 4 | 5 | 6 |
| A | 0.118 | 0.091 | 0.097 | 0.121 | 0.034 | 0.022 |
| B | 0.169 | 0.132 | 0.114 | 0.124 | 0.023 | 0.081 |
| C | 0.183 | 0.148 | 0.119 | 0.13 | 0.066 | 0.081 |
| D | 0.125 | 0.147 | 0.115 | 0.154 | 0.111 | 0.075 |
| E | 0.159 | 0.147 | 0.115 | 1.402 | 0.161 | 0.116 |
| F | 0.17 | 0.134 | 0.274 | 0.179 | 0.079 | 0.123 |
| G | 0.148 | 0.036 | 0.136 | 0.131 | 0.07 | 0.1 |
| H | 0.141 | 0.363 | 0.156 | 0.33 | 0.074 | 0.281 |

Both clones were sequenced and both showed protein-coding scFv antibodies. Overall, these results show that L1-conjugated metabolites are useful for generating metabolite-specific antibodies.

Generation of a Lateral Flow Assay Using Metabolite-Coated Gold Nanoparticles.

Figure 10:
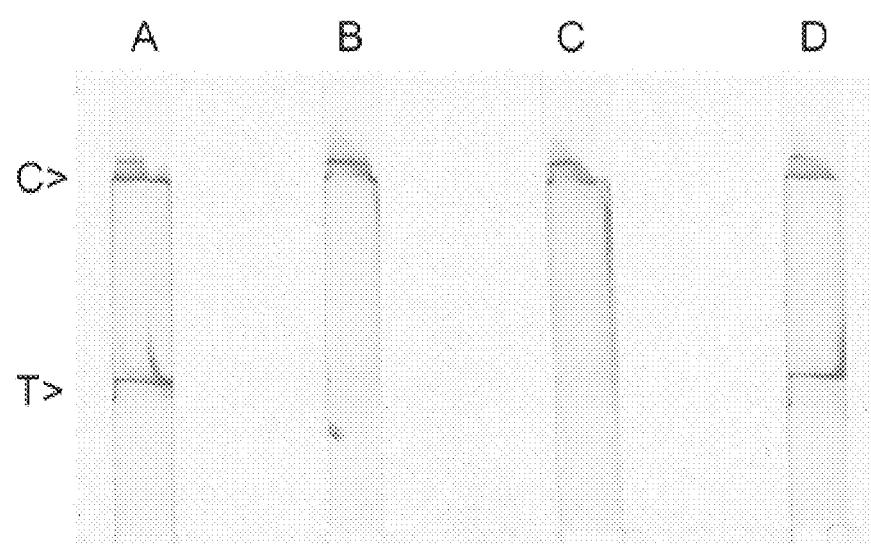
FIG. 10 depicts Lateral Flow Assays using Leucine-AuNP. Strips were loaded with Leu-AuNP solution and buffer (A); 0.5 mg/ml free Leu (B); 2 mg/ml free Leu (C) and 1M Urea (D). Test band (T) detects Leu-AuNP and Control band (C) detects Glutamate (present in our AuNP) and is not affected by the presence of other metabolites.
Figure 11:
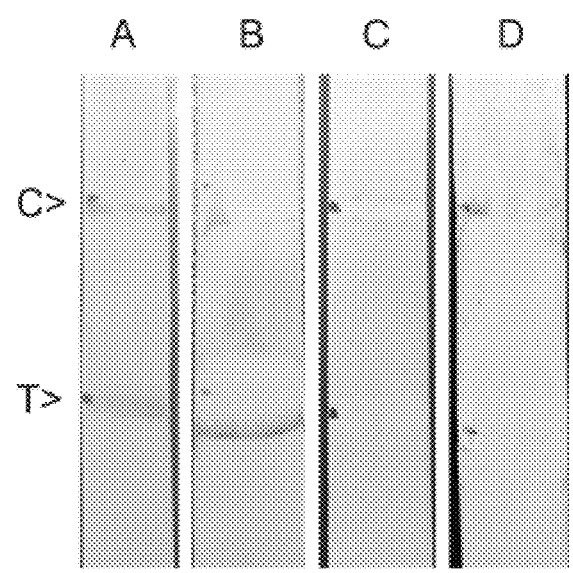
FIG. 11 depicts Specificity of Branched-chain Aminoacid Lateral Flow Assay. A) Leu-AuNP mixed with free Citrate 2 mg/ml; B) Ile-AuNP with buffer; C) L1-AuNP; D) Leu-AuNP in a strip with Myo-Inositol binding protein in the Test zone to confirm specificity of Leu-AuNP binding.

We next used the L1 linker and the L1-conjugate system for metabolite detection. We generated a useful metabolite sensor using a combination of a lateral flow assay (LFA), a metabolite-L1-AuNP conjugate (Leucine) and metabolite-specific protein. While metabolite binding antibodies can be used for metabolite detection it is also possible to use metabolite-specific binding proteins. In particular periplasmic binding proteins (PBPs) are a large and diverse class of small molecule binding proteins that are used widely by many bacteria in metabolite transport. PBPs exhibit strong and very specific affinity to a number of metabolites such as amino acids, sugars, metals and organic acids. When detecting small molecules by LFA, a competitive assay format is the most suitable configuration,[34] The principle behind a competitive LFA is known. In our assay, the branched-chain amino acid-binding protein LivF35 was loaded onto nitrocellulose strips as the detection protein ("Test band") and as the "Control band" the glutamate/aspartate binding protein Gltl36 was used, since the gold nanoparticles are stabilized with glutamate on their surface and that can be detected by Gltl as flow control. Leucine-decorated gold nanoparticles were loaded at the end of the strip in solution, with or without competing free leucine and the flow assay was performed. Our results show that the LFA strip can detect the leucine-coated AuNP, while in the presence of free leucine, this detection is abrogated (FIGS. 10 A, B and C). This indicates that our LFA is capable of detecting the presence of free target metabolite (leucine) in a mixture, and furthermore, detection capability was not hampered when other free metabolites were present in the mixture, such as urea (FIG. 10D) or citrate (FIG. 11). Isoleucine-AuNP conjugates generated with the same chemistry, were also detected by LivF (FIG. 11). As a control of specificity, when the LFA was performed in the absence of leucine, L1-AuNP no signal on the LFA. Likewise, when proteins were used that bind to different metabolites, such as Myo-inositol binding protein[37], no binding to Leucine-coated AuNP was observed (FIG. 11).

Conclusions

Metabolomics is making great advances that help improve diagnosis and understanding of disease; however, metabolomics still relies on complex, expensive and resource-consuming analytical methods. The linkers introduced in this work present a simple and innovative tool to help design new methods for metabolomics research.

A linker was successfully created through "click" chemistry, that is water soluble and that can be conjugated to different molecules by way of a terminal aldehyde. This allows the conjugation to amino acids and any amine-containing metabolite (like carnitine and carnosine). We have been able to attach three modified metabolites with thiolated linkers to AuNPs. The modified Glutamate with both linkers presents increased stability compared to the modified carnosine and Histidine that resulted in instant aggregation when added to the AuNP-citrate. However, we demonstrated that the stability of conjugated AuNPs with Glutamate can be used in double conjugation and produced two different metabolites on the surface of the AuNPs. These mixed-layer AuNP-metabolites have an exciting future for universal tags that can selectively bind target proteins, antibodies, or aptamers. These linkers can be used to modify a number of metabolites using the same approach established herein.

In this work, we showed two different uses for linker-conjugated metabolites: we used the linker to immobilize carnosine by means of its thiol terminus and use the immobilized metabolite to screen for specific antibodies using antibody phage display methods. This allowed us to obtain a pool of candidate antibodies against a small molecule, circumventing usual problems found when trying to raise polyclonal or monoclonal antibodies: having to conjugate the metabolite to carrier protein with the concomitant lack of homogeneity, variable titres and heterogeneous affinities and the risk of not having an immune response if the target molecule is similar to hosts' molecules (which is mostly the case with metabolites).

We have also developed a test to detect branched chain amino acids in a sample, by using our AuNP conjugation with Leucine and LIV binding protein LivF, to develop a lateral flow assay that can detect free Leucine in a sample in a range of conditions. This test has direct impact in human health,[38] where metabolic disorders associated with branched chain amino acid metabolism could have a better prognosis with improved diagnostic methods.

The ability to easily prepare gold-labeled metabolites permits detection including absorbance, fluorescence, surface plasm on resonance, surface-enhanced Raman spectroscopy[39] and electrical impedance.

EXPERIMENTAL SECTION

Materials.

All materials were used as received without further purification. Chloroauric acid ($HAuCl_4 \cdot 3H_2O$), trisodium citrate, tetraethylene glycol (TEG), p-toluene sulfonate (TSCI), sodium azide, potassium thioacetate, 4-dimethylamino pyridine (DMAP), sodium hydroxide, triethylamine (Et3N), copper (II) sulfatepentahydrate, benzoic acid, sodium ascorbate, oxalylchloride, sodium borohydride ($NaBH_4$), carnosine, histidine, glutamate were purchased from Sigma Aldrich. 4-pentyn-1-ol was purchased from GFS Chemicals. All solvents where purchased from Sigma Aldrich, dimethylformamide (DMF) and aceteonitrile were dried over 4 Å molecular sieves before use. Tetrahydrofuran (THF) was dried using our Pure Solv™ Micro Solvent Purification System. All water was purified using the Milli-Q® integral water purification system. Phage display libraries of human single-chain antibodies (scFv), and all necessary E. coli strains and vectors, were obtained from Source Biosciences (Cambridge, UK). Growth media and ELISA OptEIA reagents were purchased from Becton Dickinson (BD). Pierce Maleimide activated plates, clear, 8-well strips for phage display screening, bovine serum albumin (BSA) and antibody-peroxidase conjugates for ELISA assays were obtained from Thermo Fisher Scientific. High-binding MaxiSorp® plates for ELISAs were from NUNC (Sigma Aldrich).

FF80 Hi Flow nitrocellulose membranes for Lateral Flow Assay development were obtained from GE Healthcare LifeSciences.

Synthesis of Compound 5 (Tetraethylene glycol p-toluene sulfonate)

The synthesis of compound 5 was carried out following a previously established procedure[17]. Tetraethylene glycol (TEG) (90 g, 460 mmol) was dissolved in 100 mL of THF and cooled to 0° C. 2M sodium hydroxide (46 mL, 9 mmol) was then added, and stirred for 15 minutes before adding para-toluenesulfonyl chloride (11 g, 5.8 mmol). The solution was kept at 0° C. for 4 hours. 200 mL of cold water was added and stirred for 15 minutes at room temperature then extracted with dichloromethane; the aqueous layer was extracted further (3×100 mL), with the combined organic phases then washed with water and brine and dried over Na₂SO₄. After evaporation of solvent under reduced pressure the product 5 was obtained as colourless oil (20 g); reaction yield 100%. 1H NMR (600 MHz, CDCl3) δ 2.44 (s, 3H); 3.53-3.75 (m, 14H); 4.16 (t, 2H, J=7.00 Hz); 7.32 (d, 2H, J=7.5 Hz); 7.78 (d, 2H, J=7.5 Hz). 13C NMR (150, MHz, CDCl3) δ 21.7, 61.9, 68.9, 69.3, 70.5, 70.6, 70.8, 70.9, 72.6, 128.1, 129.9, 133.2, 144.9.

Synthesis of Compound 6 (Tetraethylene glycol azide)

Sodium azide (13 g, 203 mmol) was added to a solution of compound 5 in 200 mL of DMF. The reaction was heated at 60° C. for 16 hours. The reaction mixture was then filtered over celite to remove the resulting precipitate. The DMF was then removed under reduced pressure and re-dissolved in 350 mL ethyl acetate. This solution was washed with water (2×100 mL) and brine (100 mL). The organic phase was dried over Na₂SO₄ and evaporated under reduced pressure to obtain product 6 as yellow oil (13 g); reaction yield 96%. 1H NMR (600 MHz, CDCl3) δ 3.35 (t, 2H, J=7.0H); 3.57 (t, 2H, J=7.0 Hz); 3.60-3.74 (m, 14H). 13C NMR (150 MHz, CDCl3) δ 50.7; 61.8; 70.1, 70.4, 70.6, 70.7, 70.8; 72.5.

Synthesis of Compound 7 (p-toluene sulfonatetetraethyleneglycolazide)

Compound 6 was dissolved in 250 mL of dry dichloromethane and cooled to 0° C. To this solution triethylamine (15.6 mL, 111 mmol) was added and stirred for 15 minutes then para-toluenesulfonyl chloride (10.6 g, 56 mmol) was added followed by dimethylaminopyridine (DMAP) (0.05 g). The solution was allowed to warm to room temperature and stirred for 16 hours. The DCM was then washed with water (2×100 mL) and brine (100 mL) and the organic phase was dried over Na₂SO₄. The solvent was removed under reduced pressure to obtain dark yellow oil 7 (20.8 g); reaction yield 96%. 1H NMR (600 MHz, CDCl3) δ 2.44 (s, 3H); 3.37 (t, 2H, J=7.0 Hz); 3.61-3.71 (m, 12H); 4.15 (t, 2H, J=7.0); 7.32 (d, 2H, J=7.5 Hz); 7.78 (d, 2H, J=7.5). 13C NMR (150 MHz, CDCl3) δ 21.7, 50.8, 68.8, 69.4, 70.2, 70.7, 70.8, 70.9, 128.1, 129.9, 133.3, 144.9.

Synthesis of Compound 8 (Azidetetraethylene glycol thioacetate)

Potassium Thioacetate (12.2 g, 107 mmol) was added to a solution of 7 (20 g, 54 mmol) in 100 mL of acetonitrile. The reaction was stirred for 4 hours before at room temperature, a yellow precipitate was formed. Filtering off the resulting precipitate, the acetonitrile was removed under reduced pressure and the crude product was re-dissolved in DCM and washed with water (100 mL) and brine (100 mL). The organic phase was dried over Na₂SO₄ and was purified using column chromatography (ethyl acetate/hexane 1:1) to obtain 8 as dark orange oil (13 g); reaction yield 88%). 1H NMR (600 MHz, CDCl3) δ 2.33 (s, 3H); 3.09 (t, 2H, J=7.0 Hz); 3.39 (t, 2H, J=7.0 Hz); 3.57-7.71 (m, 12H). 13C NMR (150 MHz, CDCl3) δ 29.0, 30.7, 50.8, 69.9, 70.2, 70.5, 70.8, 70.9, 195.6. IR (cm-1): 2866, 2098, 1688, 1098.

Synthesis of Compound 9 (TEG-"Clicked"-Alcohol)

To a solution of compound 8 (3 g, 11 mmol) in THF/H₂O/t-butanol (1/2/1) was added 4-Pentyn-1-ol (0.91 g, 11 mmol), CuSO₄.5H₂O (0.54 g, 2 mmol), sodium ascorbic acid (0.43 g, 2 mmol), and benzoic acid (0.53 g, 4 mmol). The reaction mixture was stirred for 16 hours. THF was evaporated and 100 mL of ethyl acetate was added to the reaction mixture, washed with water (2×20 mL) and brine (30 mL). The organic phase was then dried over Na₂SO₄ and the solvent was removed by reduced pressure. The compound was then passed through a short column of silica to remove the copper traces. This compound was then oxidized to the aldehyde without purification.

Synthesis of L1 (TEG-"Clicked" aldehyde)

Oxalyl Chloride (0.85 mL, 10 mmol) was dissolved in 125 mL DCM and cooled to −78° C. To this cooled solution dimethylsulfoxide (1.53 mL, 22 mmol) was added drop-wise in 15 mL of DCM and stirred for 30 minutes. To this solution was added the alcohol 9 (3.24 g, 9 mmol) in 15 mL of DCM drop-wise over 10 minutes, and stirred for a further 1 hour at −78° C. Triethylamine (6.8 mL, 48 mmol) was then added drop-wise over 5 minutes and the solution was allowed to stir for a further 1.5 hours at −78° C. and 3 hours at room temperature. The solution was then filtered over celite and the solvent was removed under reduced pressure to yield the crude product as dark yellow oil. The product was purified using column chromatography (pure ethyl acetate) to obtain L1 as yellow oil (3 g); reaction yield 94%. 1H NMR (600 MHz, CDCl3) δ 2.34 (s, 3H); 2.82 (t, 2H, J=7.2); 2.95 (t, 2H, J=7.0); 3.00 (t, 2H, J=7.2); 3.49-3.53 (m, 10H); 3.77 (t, 2H, J=5.0); 4.42 (t, 2H, J=5.0); 7.46 (s, 1H); 9.75 (s, 1H)

Synthesis of Compound 10 (Glutamate-L1)

Sodium hydroxide (0.05 g, 1.31 mmol) was added as powder to a solution of histidine (0.175 g, 1.19 mmol) in 40 mL methanol. One spatula of MgSO4 was added to the solution once it became soluble and the aldehyde L1 (0.6 g, 1.67 mmol) in 5 mL of methanol was added drop-wise over 5 minutes. The reaction was stirred for 2 hours before adding NaBH₄ (0.06 g, 1.43 mmol) and the reaction was stirred for a further 16 hours. The solution was then filtered and reduced. The compound was re-dissolved in water and acidified to pH 4 with concentrated HCl. The solution was reduced again and extracted with ethanol, and washed again with acetone, ethyl acetate and evaporated to give the pure product 10 as a white solid (0.28 g); reaction yield 64%. 1H NMR (600 MHz, CD3OD) δ 1.86-1.89 (m, 1H); 2.09-2.15 (m, 2H); 2.54-2.56 (m, 1H); 2.61-2.63 (m, 2H); 2.82-2.88 (m, 2H); 3.14 (m, 1H); 3.57-3.61 (m, 12H); 3.70-3.72 (m, 1H); 3.87-3.89 (m, 2H); 4.31 (m, 1H); 4.53-4.56 (m, 2H); 7.89 (s, 1H). 13C NMR (150 MHz, CD3OD) δ 25.7, 27.7, 30.4, 33.3, 39.5, 42.5, 51.3, 60.7, 62.0, 70.4, 71.1, 71.4, 74.0, 146.9, 148.5, 175.1, 178.2. IR (cm-1): 3331, 2868, 1727, 1630, 1569, 1540, 1450, 1351, 1295, 1216, 1112.

Synthesis of Compound 11 (Carnosine-L1)

Sodium hydroxide (0.05 g, 1.31 mmol) was added as powder to a solution of carnosine (0.27 g, 1.19 mmol) in 40 mL of methanol. One spatula of MgSO₄ (~100 mg) was added to the solution once it became soluble and the aldehyde L1 (0.6 g, 1.67 mol) was added in 5 mL of methanol drop-wise over 5 minutes. The reaction was stirred for 2 hours before adding NaBH₄ (0.06 g, 1.43 mmol) and the reaction was stirred for a further 16 hours. The solution was then filtered and reduced. The compound was re-dissolved in water and acidified to pH 4 with concentrated HCl. The solution was reduced again and extracted with ethanol, and washed again with acetone, ethyl acetate and evaporated to give the pure product 11 as a white solid (0.39 g), reaction yield 62%.1H NMR (600 MHz, CD3OD) δ 1.86-1.89 (m, 2H); 2.02-2.06 (m, 2H); 2.63 (t, 2H, J=7.5 Hz); 2.76 (t, 2H, J=7.5 Hz); 2.82 (t, 1H, J=7.5 Hz); 2.86 (t, 1H, J=76.5 Hz); 3.08-3.12 (m, 2H); 3.24-3.27 (m, 2H); 3.58-3.63 9 m, 12H); 3.70 (t, 1H, J=7.5 Hz); 3.86-3.89 (m, 2H); 7.31 (s, 1H); 7.79 (s, 1H); 7.87 (s, 1H); 8.47 (br s, 1H). 13C NMR (150 MHz, CD3OD) δ24.6, 24.7, 26.8, 29.0, 31.0, 32.2, 33.0, 33.3, 37.1, 39.5, 45.0, 62.0, 70.4, 71.1, 74.0, 117.0, 124.0, 124.4, 135.2, 146.9, 148.5, 171.7. IR (cm-1): 3340, 2939, 2872, 1648, 1438, 1114. EA: C, 49.90; H, 7.06; N, 18.60; 0, 18.55; S, 5.89.

Synthesis of Compound 12 (Histidine-L1)

Sodium hydroxide (0.05 g, 1.31 mmol) was added as powder to a solution of histidine (0.18 g, 1.19 mmol) in 40 mL methanol. One spatula of MgSO4 was added to the solution once it became soluble and the aldehyde L1 (0.6 g, 1.67 mmol) in 5 mL of methanol was added drop-wise over 5 minutes. The reaction was stirred for 2 hours before adding NaBH4 (0.06 g, 1.43 mmol) and the reaction was stirred for a further 16 hours. The solution was then filtered and reduced. The compound was re-dissolved in water and acidified to pH 4 with concentrated HCl. The solution was reduced again and extracted with ethanol, and washed again with acetone, ethyl acetate and evaporated to give the pure product 12 as a white solid (0.34 g); reaction yield 63%. 1H NMR (600 MHz, CD3OD) δ 1.85-1.88 (m, 2H, J=7.0 Hz); 2.06-2.09 (m, 2H); 2.62-2.88 (m, 4H); 3.10-3.13 (m, 2H); 3.26-3.33 (m, 2H); 3.56-3.61 (m, 10H); 3.84 (m, 2H); 4.52-4.56 (m, 2H); 7.23 (s, 1H); 7.79 (s, 1H); 7.87 (s, 1H); 8.454 (br s, 1H). 13C NMR (150 MHz, CD3OD) δ 23.0, 25.6, 26.6, 32.4, 39.5, 49.0, 52.0, 53.3, 56.7, 61.5, 69.6, 70.1, 71.2, 71.3, 71.4, 71.5, 119.6, 125.4, 129.4, 135.6, 146.2, 169.6 IR (cm-1): 3340, 2939, 2872, 1648, 1438, 1114.

Synthesis of Compound 13 (Leucine-L1)

Sodium hydroxide (0.05 g, 1.31 mmol) was added as powder to a solution of Leucine (0.16 g, 1.19 mmol) in 40 mL methanol. One spatula of MgSO4 was added to the solution once it became soluble and the aldehyde L1 (0.6 g, 1.67 mmol) in 5 mL of methanol was added drop-wise over 5 minutes. The reaction was stirred for 2 hours before adding NaBH4 (0.06 g, 1.43 mmol) and the reaction was stirred for a further 16 hours. The solution was then filtered and reduced. The compound was re-dissolved in water and acidified to pH 4 with concentrated HCl. The solution was reduced again and extracted with ethanol, and washed again with acetone, ethyl acetate and evaporated to give the pure product 13 as a white solid (0.30 g); reaction yield 63%. 1H NMR (600 MHz, CD3OD) δ 1.85-1.88 (m, 2H, J=7.0 Hz); 2.06-2.09 (m, 2H); 2.62-2.88 (m, 4H); 3.10-3.13 (m, 2H); 3.26-3.33 (m, 2H); 3.56-3.61 (m, 10H); 3.84 (m, 2H); 4.52-4.56 (m, 2H); 7.23 (s, 1H); 7.79 (s, 1H); 7.87 (s, 1H); 8.454 (br s, 1H). 13C NMR (150 MHz, CD3OD) δ 23.0, 25.6, 26.6, 32.4, 39.5, 49.0, 52.0, 53.3, 56.7, 61.5, 69.6, 70.1, 71.2, 71.3, 71.4, 71.5, 119.6, 125.4, 129.4, 135.6, 146.2, 169.6 IR (cm-1): 3340, 2939, 2872, 1648, 1438, 1114.

Synthesis of Metabolite-L1-IAF 0.012 mmol of valine, isoleucine or glutamate, conjugated to the linker-1 was dissolved in 1 ml water. 0.012 mmol of fluorescein dye (IAF) was also added to 1 ml of DMF and added to the metabolite-Linker-1 solution. The pH of the reaction was adjusted at 8.5 using Tris buffer and stirred for 30 minutes at room temperature. The product was purified by using HPLC and the chemical structure of the compound was confirmed by mass spectrometry.

NMR Spectroscopy.

$^1$H NMR and $^{13}$C NMR was done using a Varian Innova two-channel 600 MHz spectrometer. $^{13}$C NMR was done using both direct and indirect detection of $^{13}$C nuclei.

UV Visible Spectroscopy (UV-VIS).

UV-Vis spectra were recorded at room temperature with an Agilent 8453 instrument in the 400-620 nm range using 1-cm path length quartz cuvettes and 1.5 nm bandwidth. The UV-VIS spectrum of AuNP-citrate shows an intense resonance band, centered at 522 nm, in the spectrum of AuNP-citrate. Upon addition of modified metabolites to the AuNPs we see a shift in the resonance band, between 523-526 nm.

Dynamic Light Scattering (DLS).

Particle Size Distribution was measured by Dynamic Light Scattering (DLS). Measurements were obtained with a Malvern Zetasizer Nano-ZS instrument with temperature control. Each sample was recorded at 25° C.±1° C., in triplicate; each measurement was the average of 12 data sets acquired for 20 seconds each. Hydrodynamic diameters have been calculated using the internal software analysis from the DLS intensity-weighted particle size distribution.

Scanning Electron Microscopy (SEM).

SEM imaging was done using the Zeiss Sigma 300 VP-FESEM. Each sample was measured to give a 3-D representation of the particle size distribution to correlate with our DLS measurements.

Preparation of Stabilized Metabolite-modified AuNPs.

The synthesis of ~20 nm colloidal AuNPs was done using trisodium citrate (Na3C6H5O7) reduction of chloroauric acid (HAuCl4) to form gold nanoparticles. 45 The concentration of citrate and chloroauric acid, along with the reaction time strongly influences the size and size distribution of the AuNPs. Trisodium citrate and chloroauric acid stock solutions were made using ultrapure water. Production of 20 nm gold nanoparticles was done by placing 800 mL of (0.01% w/w) solution in a 1 L round-bottom flask and stirred for 20 minutes at reflux. Next 24 mL of (1% w/w) solution of trisodium citrate was added and stirred for a further 25 minutes. Upon addition of the citrate the solution turned from yellow to clear to red. The reaction was allowed to cool to room temperature and stored overnight at 4° C. The gold citrate solution was filtered into brown glass bottles to protect from visible light and remove any solid aggregates, and then stored in the refrigerator at 4° C. After 2 months the gold citrate solution began forming solid aggregates, at this point, the solution was disposed of.

The synthesis of L1-conjugated metabolites to gold was done in a 20 mL vial at room temperature under nitrogen flow. Starting with 5 mL of AuNP citrate solution (~0.25 mg of gold) 500 μL of the modified metabolite solution (0.8 mM in water) and stirred for 8 hours, the solution was placed in 50 mL centrifuge tubes along with 15 mL of ultrapure water and centrifuged at 10000 RPM. The supernatant was then removed and the gold colloid was re-suspended 20 mL of ultrapure water and centrifuged again. The gold conjugate pellets were then re-suspended in 6 mL of ultra-pure water, yielding a lighter red solution than previously seen before modification. The AuNP-metabolite conjugates were then placed in 15 mL disposable centrifuge tubes and stored at 4° C. until further analysis.

Phage Display Screening for Metabolite-Binding Antibodies (scFv):

Phage display libraries were prepared following manufacturer's instructions according to published methods[46]. Linker-coupled metabolites were immobilized on maleimide-coated plates by incubating metabolite solution in binding buffer overnight at 4° C. after 2 washes. Following incubation, 3 more washes were done, followed by a 1 hour incubation with cysteine solution (10 ug/mL) in binding buffer, to block free maleimide groups. General blocking was done by incubating metabolite-coated plates with 2% BSA in PBS buffer overnight at 4° C.

ScFv libraries where prepared in a BSA 2% solution in PBS buffer to a titre of 1012, then incubated on metabolite-coated plates for 1 hour at room temp with gentle rocking. Afterwards, washed 10-20 times with PBS (increasing number of washes with each round of panning) and bound scFv-harboring phages were eluted incubating with 1 mg/mL trypsin for 1 hour. Phages encoding selected antibodies were used to infect susceptible TG1 E. coli cells.

Infected cells were plated in TYE-Ampicillin plates and recovered phage titres were estimated by plating serial dilutions to confirm that expected amount of phage was selected. Colonies from each selection round were used to produce the library phage that was used in the following round. After 3 rounds of panning, individual clones were used in ELISAs to detect specific binders, as described by manufacturers. ELISAs were performed in standard 96-well plates, using L1-carnosine, and then blocking with 2% Bovine Serum Albumin (BSA), or just Blocking with BSA to detect nonspecific binding. Strong binding scFv-phages were detected with a peroxidase-coupled anti M13 antibody and color development was measured at 405 nm using a Thermomax Plate reader (Molecular Devices). A ubiquitin positive control phage was provided by the manufacturer, bovine ubiquitin (Sigma) in PBS (90 µg/ml) was used as directed in the manual as a positive control.

Lateral Flow Assay for Metabolite Detection:

Periplasmic binding protein sequences from *E. coli* were obtained from databases (uniprot.org) and synthetic gene-coding DNA was ordered from DNA 2.0 cloned into pET15b expression vector (Novagen, EMD-Millipore). Constructs were transformed into *E. coli* BL21 for protein expression. The recombinant branched-chain amino acid binding protein LivF and the glutamate/aspartate binding protein GltI were expressed and purified above 95% purity using Ni-NTA agarose matrix according to the manufacturer's descriptions (Qiagen, The Expressionist). Briefly, 1 L cultures of bacteria harboring LivF or GltI coding genes in pET15b plasmids were harvested after overnight induction at 30° C. The periplasmic fraction was extracted by osmotic shock[47] and the resulting fluid (which contained the recombinant protein) was equilibrated with phosphate buffer (50 mM pH 7.5), NaCl (150 mM) and imidazole (10 mM) to match the requirements for NTI-Agarose nickel affinity chromatography columns (Qiagen). The protein solutions were loaded, washed with 50 mM imidazole for 20 column volumes and eluted with 250 mM imidazole (5 column volumes), then buffer was exchanged using dialysis with 3 solvent exchanges in phosphate buffer (50 mM pH 7.5) for at least 4 hours each time. The protein was quantified both by UV absorbance at 280 nm and assessed for purity and quantity using SDS-PAGE with a sample loading of 10 ug. The SDS-PAGE was used to check for impurities of up to 1%. To prepare the LFA strips, 1ug of each protein (from a 0.5 ug/ul solution in 50 mM phosphate buffer, pH 7.5) was loaded onto FF80 nitrocellulose strips as a 0.5 cm line. 20 ul of a suspension of metabolite-coated AuNPs (3 mg/mL) was loaded onto the end of the membrane strips and allowed to flow through via capillary action. Bands showing the captured gold nanoparticles were documented with an electronic flatbed scanner (Canon Canoscan 5600).

REFERENCES (1) Koulman, A.; Lane, G. A.; Harrison, S. J.; Volmer, D. A. From Differentiating Metabolites to Biomarkers. Anal. Bioanal. Chem.2009, 394, 663-670.

(2) Fonteh, A. N.; Harrington, R. J.; Tsai, A.; Liao, P.; Harrington, M. G. Free Amino Acid and Dipeptide Changes in the Body Fluids from Alzheimer's Disease Subjects. Amino Acids 2007, 32, 213-224.

(3) Alzheimer; Association. 2014 Alzheimer's Disease Facts and Figures Includes a Special Report on Women and Alzheimer's Disease.

(4) RACHAKONDA, V.; PAN, T. H.; LE, W. D. Biomarkers of Neurodegenerative Disorders: How Good Are They? Cell Res.2004, 14, 349-358.

(5) Fracchiolla, N. S.; Artuso, S.; Cortelezzi, A. Biosensors in Clinical Practice: Focus on Oncohematology. Sensors (Basel).2013, 13, 6423-6447.

(6) Wang, J.; Chatrathi, M. P.; Ibañez, A. Glucose Biochip: Dual Analyte Response in Connection to Two Pre-Column Enzymatic Reactions. Analyst 2001, 126, 1203-1206.

(7) Bergmeyer, H. U.; Gawehn, K. Methods of Enzymatic Analysis Volume 2; Verlag Chemie, 2012.

(8) Volkov, A.; Mauk, M.; Corstjens, P.; Niedbala, R. S. Rapid Prototyping of Lateral Flow Assays. Methods Mol. Biol.2009, 504, 217-235.

(9) Liu, C.; Jia, Q.; Yang, C.; Qiao, R.; Jing, L.; Wang, L.; Xu, C.; Gao, M. Lateral Flow lmmunochromatographic Assay for Sensitive Pesticide Detection by Using Fe3O4 Nanoparticle Aggregates as Color Reagents. Anal. Chem.2011, 83, 6778-6784.

(10) Ngom, B.; Guo, Y.; Wang, X.; Bi, D. Development and Application of Lateral Flow Test Strip Technology for Detection of Infectious Agents and Chemical Contaminants: A Review. Anal. Bioanal. Chem.2010, 397, 1113-1135.

(11) Zhang, G. P.; Wang, X. N.; Yang, J. F.; Yang, Y. Y.; Xing, G. X.; Li, Q. M.; Zhao, D.; Chai, S. J.; Guo, J. Q. Development of an lmmunochromatographic Lateral Flow Test Strip for Detection of Beta-Adrenergic Agonist Clenbuterol Residues. J. Immunol. Methods 2006, 312, 27-33.

(12) Tang, D.; Sauceda, J. C.; Lin, Z.; Ott, S.; Basova, E.; Goryacheva, 1.; Biselli, S.; Lin, J.; Niessner, R.; Knopp, D. Magnetic Nanogold Microspheres-Based Lateral-Flow Immunodipstick for Rapid Detection of Aflatoxin B2 in Food. Biosens. Bioelectron.2009, 25, 514-518.

(13) Taranova, N. A.; Byzova, N. A.; Zaiko, V. V.; Starovoitova, T. A.; Vengerov, Y. Y.; Zherdev, A. V.; Dzantiev, B. B. Integration of Lateral Flow and Microarray Technologies for Multiplex Immunoassay: Application to the Determination of Drugs of Abuse. Microchim. Acta 2013, 180, 1165-1172.

(14) Singh, K. V; Kaur, J.; Varshney, G. C.; Raje, M.; Suri, C. R. Synthesis and Characterization of Hapten-Protein Conjugates for Antibody Production against Small Molecules. Bioconjug. Chem.15, 168-173.

(15) Posthuma-Trumpie, G. A.; Korf, J.; van Amerongen, A. Lateral Flow (Immuno)assay: Its Strengths, Weaknesses, Opportunities and Threats. A Literature Survey. Anal. Bioanal. Chem.2009, 393, 569-582.

(16) Rosen, S. Market Trends in Lateral Flow Immunoassays. In Lateral Flow Immunoassay; Humana Press: Totowa, N.J., 2009; pp. 1-15.

(17) Smet, M.; Dehaen, W. Synthesis of Crown Ethers Containing a Rubicene Moiety. Molecules 2000, 5, 620-628.

(18) Ojea-Jiménez, I.; Garcia-Fernandez, L.; Lorenzo, J.; Puntes, V. F. Facile Preparation of Cationic Gold Nanoparticle-Bioconjugates for Cell Penetration and Nuclear Targeting. ACS Nano 2012, 6, 7692-7702.

(19) Kolb, H. C.; Finn, M. G.; Sharpless, K. B. Click Chemistry: Diverse Chemical Function from a Few Good Reactions. Angew. Chem. Int. Ed. Engl.2001, 40, 2004-2021.

(20) Boisselier, E.; Salmon, L.; Ruiz, J.; Astruc, D. How to Very Efficiently Functionalize Gold Nanoparticles by " click" Chemistry. Chem. Commun. (Camb). 2008, 5788-5790.

(21) Shukla, R.; Bansal, V.; Chaudhary, M.; Basu, A.; Bhonde, R. R.; Sastry, M. Biocompatibility of Gold Nanoparticles and Their Endocytotic Fate inside the Cellular Compartment: A Microscopic Overview. Langmuir 2005, 21, 10644-10654.

(22) Abdel-Magid, A. F.; Carson, K. G.; Harris, B. D.; Maryanoff, C. A.; Shah, R. D. Reductive Amination of Aldehydes and Ketones with Sodium Triacetoxyborohydride. Studies on Direct and Indirect Reductive Amination Procedures (1). J. Org. Chem.1996, 61, 3849-3862.

(23) Saha, K.; Agasti, S. S.; Kim, C.; Li, X.; Rotello, V. M. Gold Nanoparticles in Chemical and Biological Sensing. Chem. Rev.2012, 112, 2739-2779.

(24) Jain, K. K. Current Status of Molecular Biosensors. Med. Device Technol.2003, 14, 10-15.

(25) Agasti, S. S.; Rana, S.; Park, M.-H.; Kim, C. K.; You, C.-C.; Rotello, V. M. Nanoparticles for Detection and Diagnosis. Adv. Drug Deliv. Rev.2010, 62, 316-328.

(26) Zhao, P.; Li, N.; Salmon, L.; Liu, N.; Ruiz, J.; Astruc, D. How a Simple clicked" PEGylated 1,2,3-Triazole Ligand Stabilizes Gold Nanoparticles for Multiple Usage. Chem. Commun. Chem. Commun 2013, 49, 3218-3220.

(27) Lund, T.; Callaghan, M. F.; Williams, P.; Turmaine, M.; Bachmann, C.; Rademacher, T.; Roitt, I. M.; Bayford, R. The Influence of Ligand Organization on the Rate of Uptake of Gold Nanoparticles by Colorectal Cancer Cells. Biomaterials 2011, 32, 9776-9784.

(28) Schulz, F.; Vossmeyer, T.; Bastús, N. G.; Weller, H. Effect of the Spacer Structure on the Stability of Gold Nanoparticles Functionalized with Monodentate Thiolated Poly(ethylene Glycol) Ligands. Langmuir 2013, 29, 9897-9908.

(29) Turkevich, J.; Stevenson, P. C.; Hillier, J. A Study of the Nucleation and Growth Processes in the Synthesis of Colloidal Gold. Discuss. Faraday Soc.1951, 11, 55.

(30) Zakaria, H. M.; Shah, A.; Konieczny, M.; Hoffmann, J. A.; Nijdam, A. J.; Reeves, M. E. Small Molecule- and Amino Acid-Induced Aggregation of Gold Nanoparticles. Langmuir 2013, 29, 7661-7673.

(31) Gold Nanoparticles: Properties and Applications I Sigma-Aldrich http://www.sigmaaldrich.com/materials-science/nanomaterials/gold-nanoparticles.html.

(32) Zhong, Z.; Patskovskyy, S.; Bouvrette, P.; Luong, J. H. T.; Gedanken, A. The Surface Chemistry of Au Colloids and Their Interactions with Functional Amino Acids. J. Phys. Chem. B2004, 108, 4046-4052.

(33) Bishop, J. E.; Squier, T. C.; Bigelow, D. J.; Inesi, G. (Iodoacetamido)fluorescein Labels a Pair of Proximal Cysteines on the Ca2+-ATPase of Sarcoplasmic Reticulum. Biochemistryl 988, 27, 5233-5240.

(34) Tobergte, D. R.; Curtis, S. Lateral Flow Immunoassay; Wong, R.; Tse, H., Eds.; 2013; Vol. 53.

(35) Adams, M. D.; Wagner, L. M.; Graddis, T. J.; Landick, R.; Antonucci, T. K.; Gibson, A. L.; Oxender, D. L. Nucleotide Sequence and Genetic Characterization Reveal Six Essential Genes for the LIV-I and LS Transport Systems of Escherichia Coli. J. Biol. Chem.1990, 265, 11436-11443.

(36) Willis, R. C.; Furlong, C. E. Interactions of a Glutamate-Aspartate Binding Protein with the Glutamate Transport System of Escherichia Coli. J. Biol. Chem.1975, 250, 2581-2586.

(37) Herrou, J.; Crosson, S. Myo-Inositol and D-Ribose Ligand Discrimination in an ABC Periplasmic Binding Protein. J. Bacteriol. 2013, 195, 2379-2388.

(38) Burrage, L. C.; Nagamani, S. C. S.; Campeau, P. M.; Lee, B. H. Branched-Chain Amino Acid Metabolism: From Rare Mendelian Diseases to More Common Disorders. Hum. Mol. Genet.2014, 23, R1-8.

(39) Hwang, J.; Lee, S.; Choo, J.; Liu, C.; Jia, Q.; Yang, C.; Qiao, R.; Jing, L.; Wang, L.; Xu, C.; et al. Application of a SERS-Based Lateral Flow Immunoassay Strip for the Rapid and Sensitive Detection of Staphylococcal Enterotoxin B. Nanoscale 2016, 8, 11418-11425.

(40) Carrio, A.; Sampedro, C.; Sanchez-Lopez, J. L.; Pimienta, M.; Campoy, P. Automated Low-Cost Smartphone-Based Lateral Flow Saliva Test Reader for Drugs-of-Abuse Detection. Sensors (Basel).2015, 15, 29569-29593.

(41) Cadle, B. A.; Rasmus, K. C.; Varela, J. A.; Leverich, L. S.; O'Neill, C. E.; Bachtell, R. K.; Cooper, D. C. Cellular Phone-Based Image Acquisition and Quantitative Ratiometric Method for Detecting Cocaine and Benzoylecgonine for Biological and Forensic Applications. Subst. Abuse 2010, 4, 21-33.

(42) Spyrou, E. M.; Kalogianni, D. P.; Tragoulias, S. S.; Ioannou, P. C.; Christopoulos, T. K. Digital Camera and Smartphone as Detectors in Paper-Based Chemiluminometric Genotyping of Single Nucleotide Polymorphisms. Anal. Bioanal. Chem.2016.

(43) Global Observatory for eHealth series; World Health Organization. mHealth New Horizons for Health through Mobile Technologies.

(44) Lai, J. J.; Stayton, P. S. Improving Lateral-Flow Immunoassay (LFIA) Diagnostics via Biomarker Enrichment for mHealth. Methods Mol. Biol.2015, 1256, 71-84.

(45) Baranov, D.; Kadnikova, E. N.; Daniel, M. C.; Astruc, D.; Liz-Marzan, L. M.; Stewart, M. E.; Anderton, C. R.; Thompson, L. B.; Maria, J.; Gray, S. K.; et al. Synthesis and Characterization of Azidoalkyl-Functionalized Gold Nanoparticles as Scaffolds for "click"-Chemistry Derivatization. J. Mater. Chem.2011, 21, 6152.

(46) Lee, C. M.; Iorno, N.; Sierro, F.; Christ, D. Selection of Human Antibody Fragments by Phage Display. Nat Protoc 2007, 2, 3001-3008.

(47) Bowden, G. A.; Georgiou, G. Folding and Aggregation of Beta-Lactamase in the Periplasmic Space of Escherichia Coli. J. Biol. Chem.1990, 265, 16760-16766.

Example 2

Figure 2B:
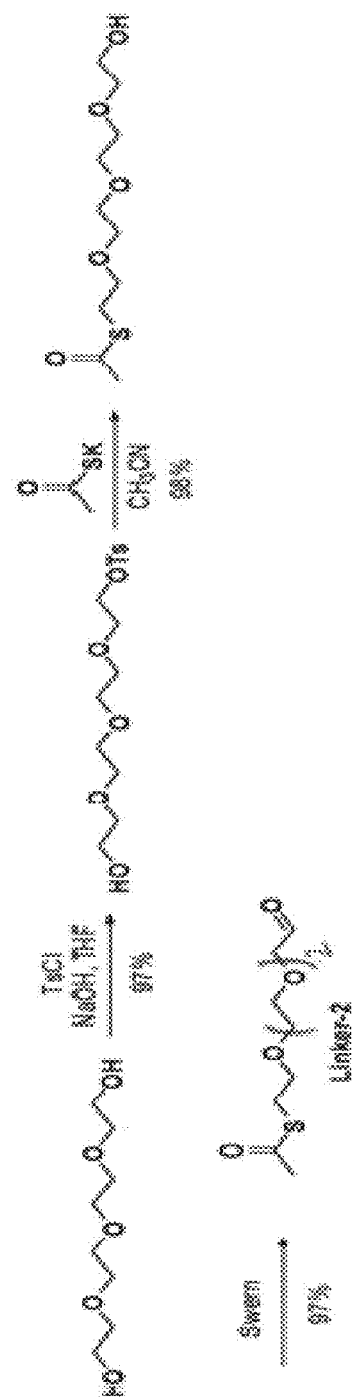
FIG. 2B depicts synthesis of Linker-2 in 3 steps from tetraethylene glycol.
Figure 2C:
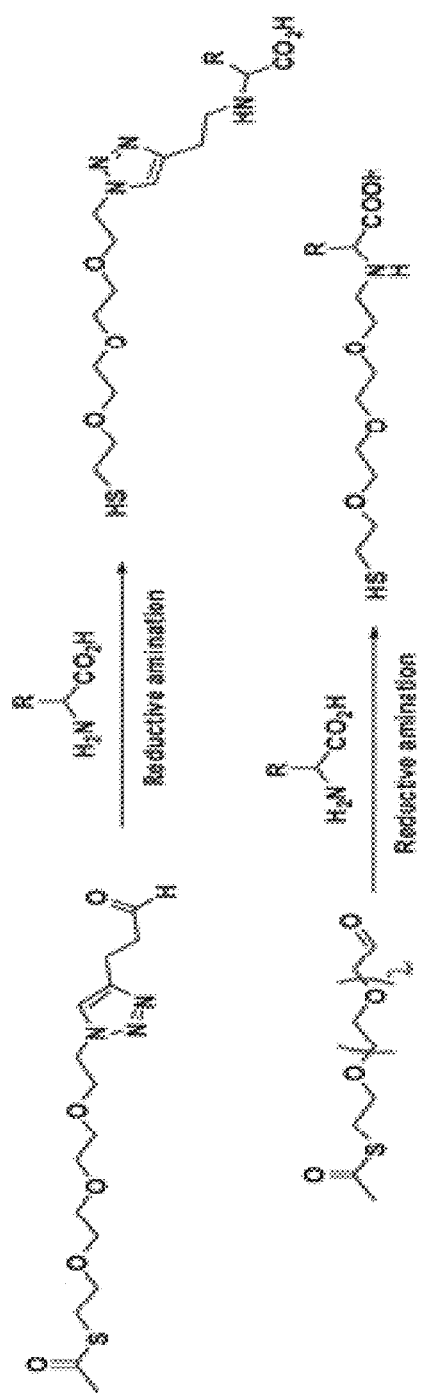
FIG. 2C depicts reductive animation.
Figure 3A:
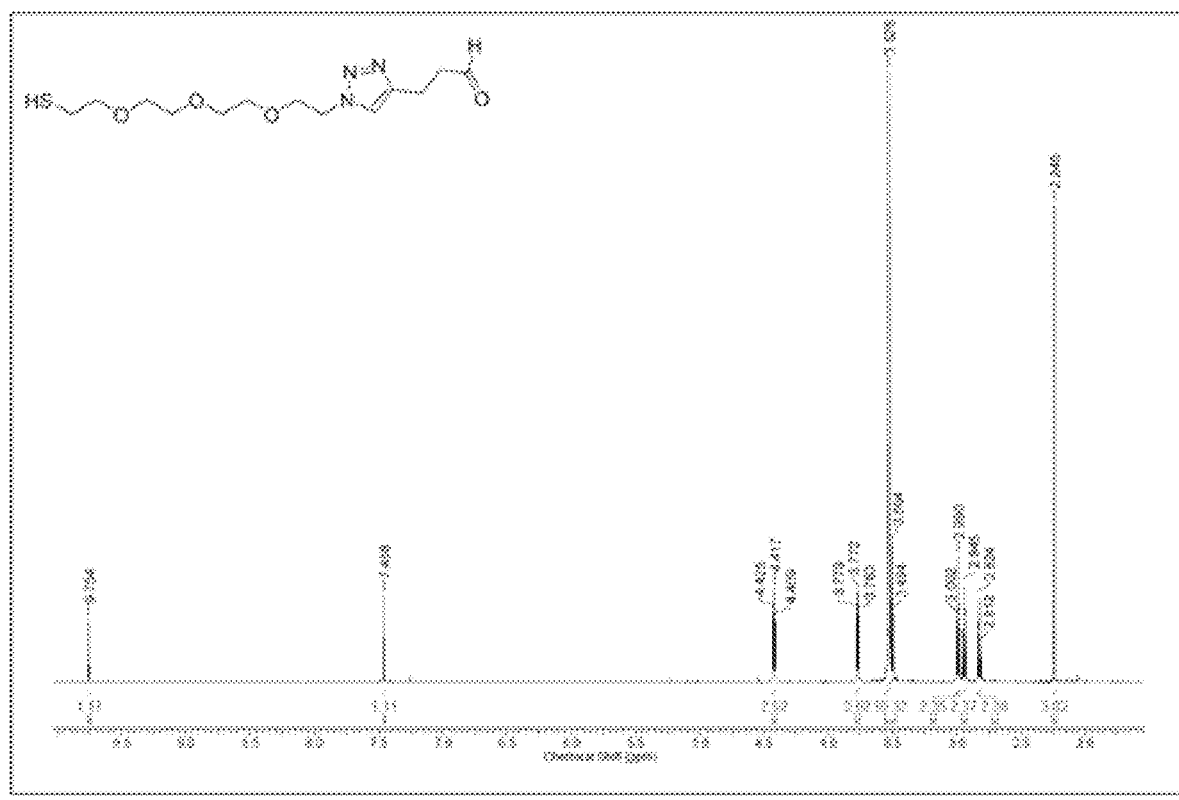
FIG. 3A-G depicts confirmation of L1 synthesis was demonstrated by Nuclear Magnetic Resonance (NMR) showing chemical shifts that confirm its structure by detection of either H1 or C13 nuclei. $^1$H NMR was done using a Varian Inova 600 MHz spectrometer. $^{13}$C NMR was done using a Varian VNMRS two-channel 600 MHz Spectrometer, which possess direct and indirect detection of $^{13}$C nuclei.
Figure 3B:
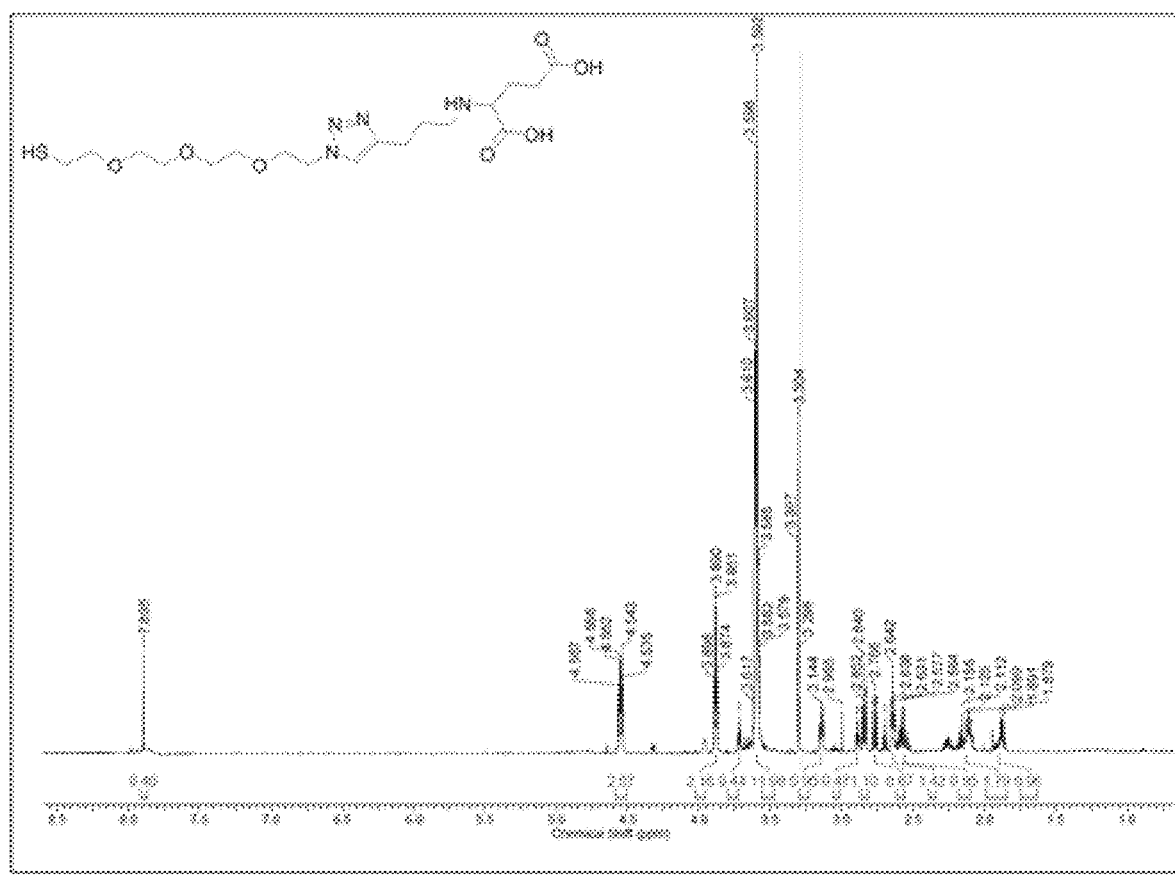
Figure 3C:
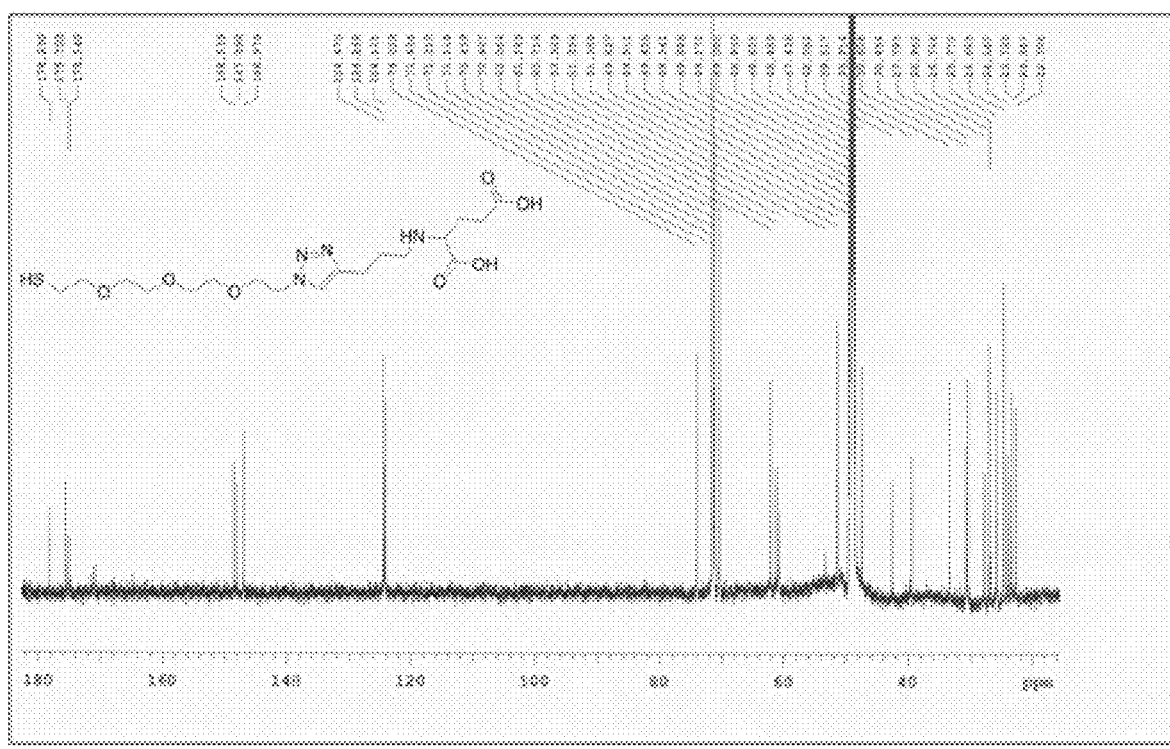
Figure 3D:
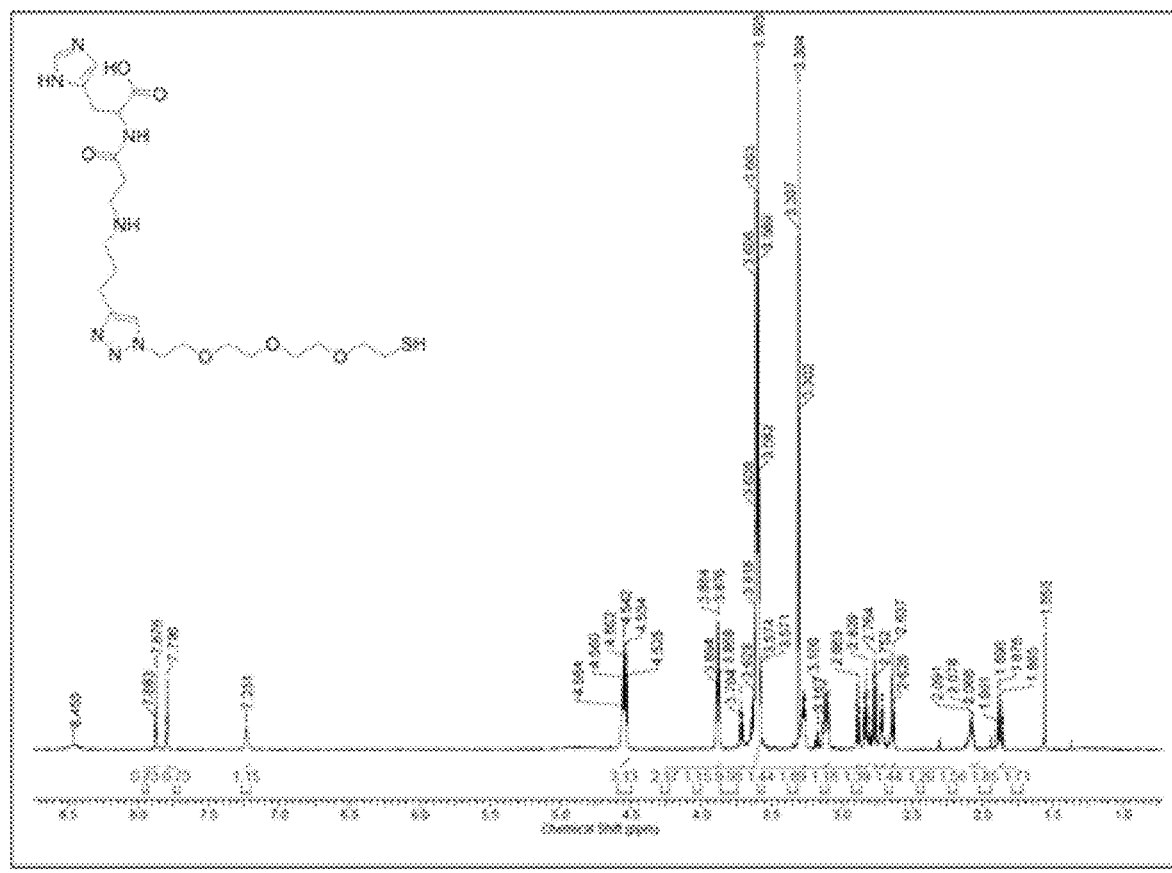
Figure 3E:
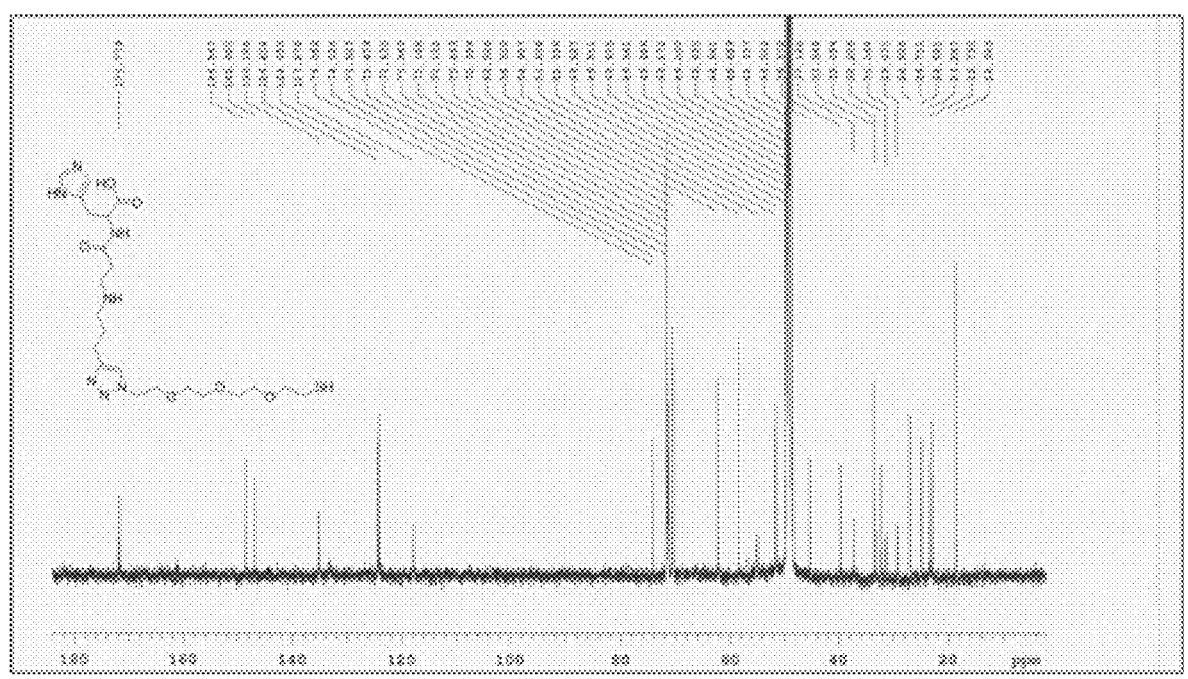
Figure 3F:
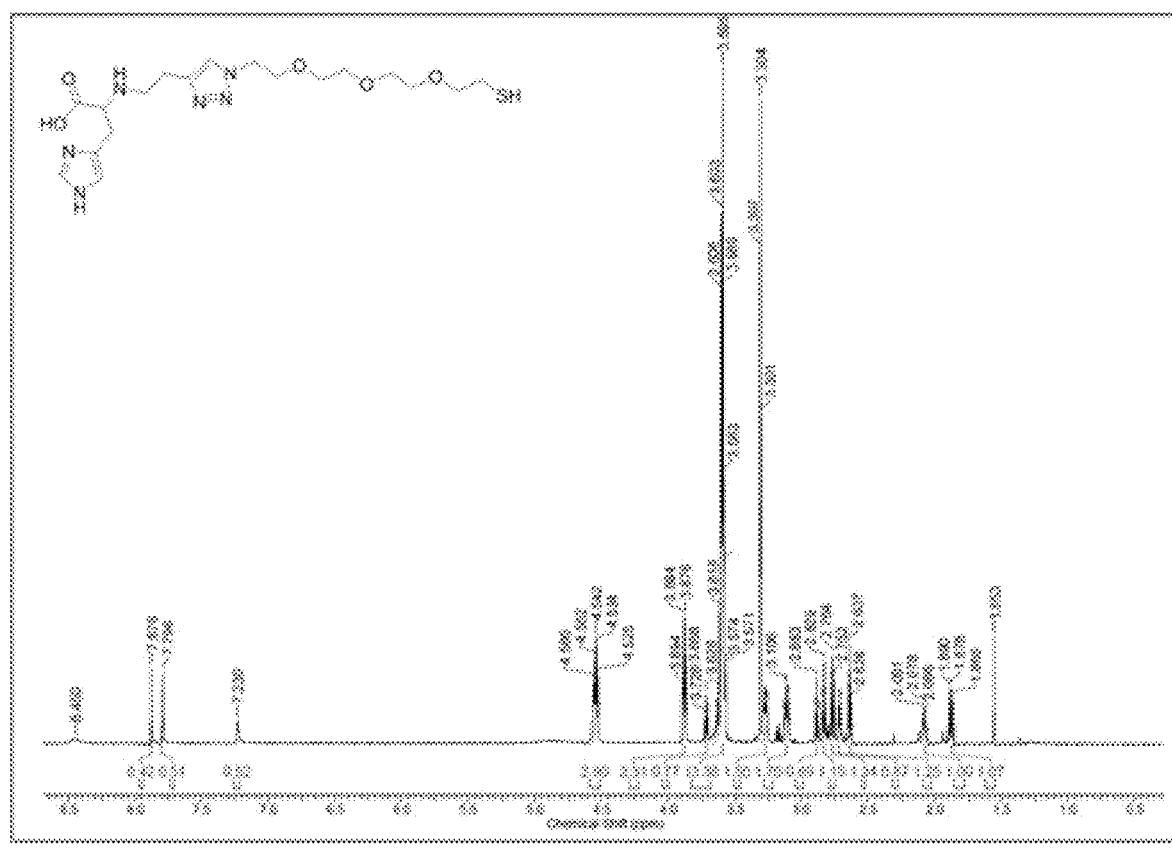
Figure 3G:
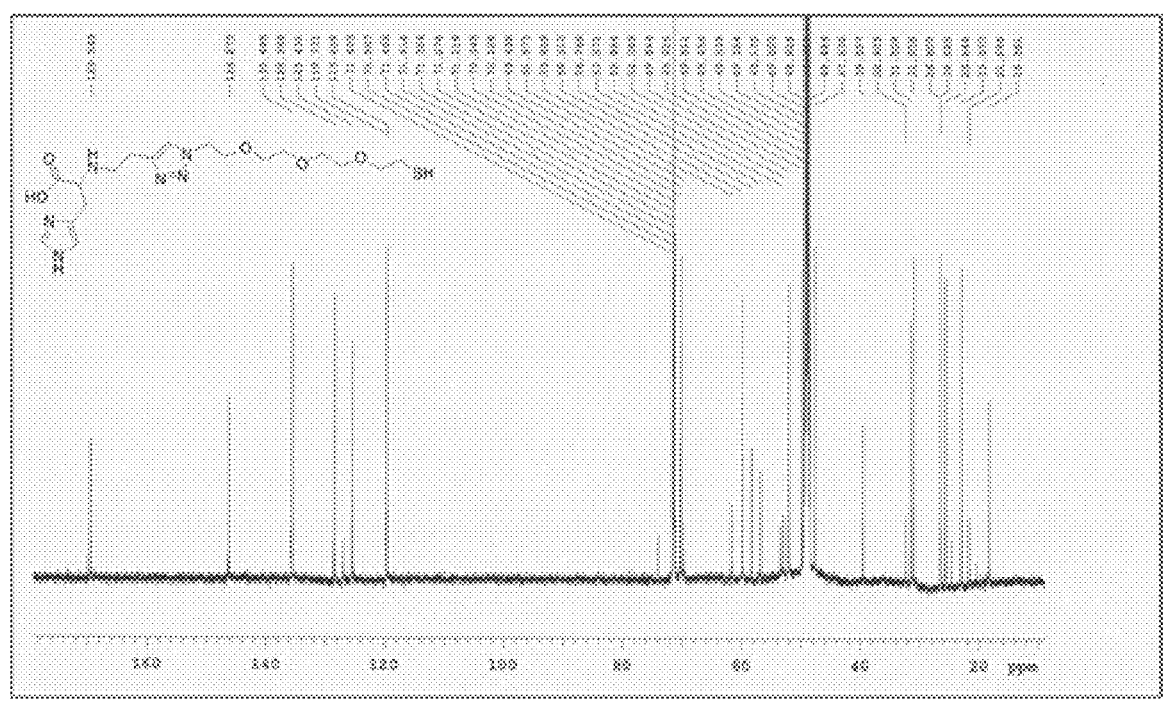

In another example, a second linker, Linker-2, has been synthesized in three steps, starting from tetraethylene glycol and it is shorter than linker-1 and doesn't contain a triazole cycle (FIG. 2B).

These two linkers can attach in the same way to the metabolite of interest, and the different chain lengths allow the metabolites versatility during biorecognition studies, without compromising stability or solubility.

For the Linker-2, tetraethylene glycol was tosylated and then treated by potassium thioacetate to introduce the thiol group and then the primary alcohol was oxidized to the aldehyde in quantitative yield by using Swern oxidation (FIG. 2B).

Figure 12:
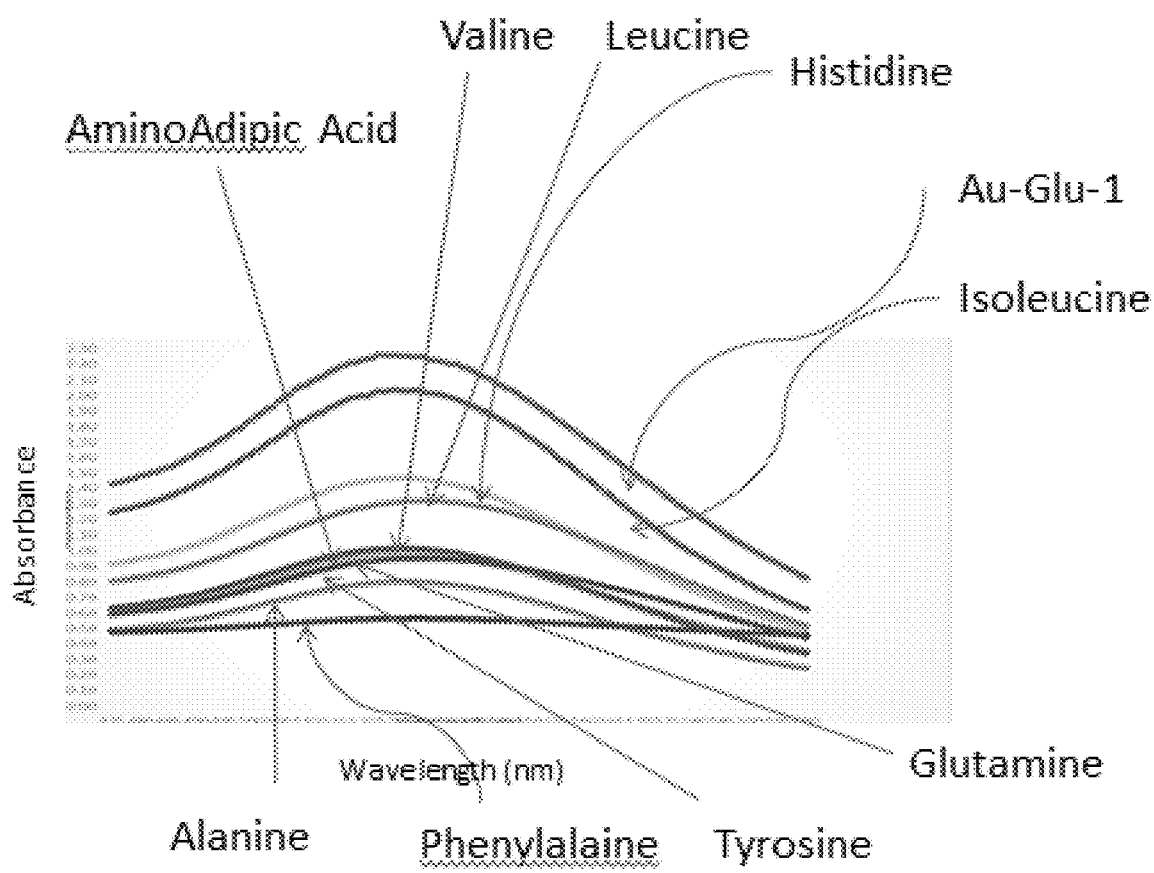

FIG. 12 shows UV-Vis Spectra of double conjugated AuNPs with modified aminoacids-linker-1.

Figure 13:
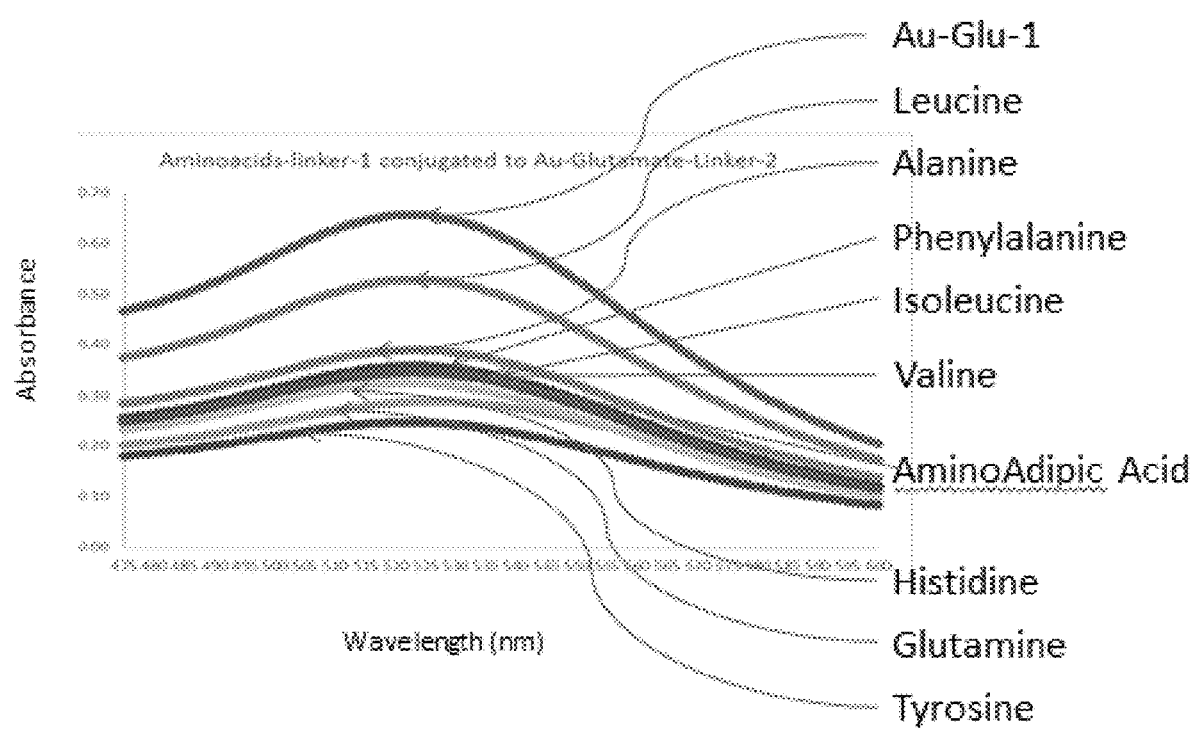
FIG. 13 shows UV-Vis Spectra of double conjugated AuNPs-Linker-2-Glutamate Using modified aminoacids with both linker-1.

As it shown in the FIG. 13, the UV-Vis spectra shows a slight shift of the absorbance curve (3 to 7 nm), which demonstrates the double conjugation of the AuNPs and it occurs with just a small increase in AuNP size.

We designed and synthesized a new linker (linker-2), which doesn't contain a triazole ring. We then modified all thirteen aminoacids with the new linker (linker-2) using reductive amination reaction between the primary amine of aminoacids and the aldehyde moiety of the linker. Except for Carnosine, Lysine and Ornithine, they were attached from the primary amine of the alkyl chain.

After testing all thirteen aminoacids with AuNPs citrate, we obtained the same results as with metabolites-linker-1, the aggregation of AuNPs was observed in the case of all the same 8 amino acids (Leucine, Isoleucine, Phenylalanine, Tyrosine, Histidine, Carnosine, Lysine and Ornithine) that gave aggregation when they are modified with linker-1. This removes any doubt that the triazole played any role in the aggregation of the AuNPs during the conjugation of AuNPs-Citrate.

We stabilized AuNPs citrate with modified-glutamate-linker-2 and used it in the double conjugate process for all thirteen aminoacids.

The UV-vis spectra presented in FIG. 13, shows that when adding modified aminoacids with linker-1 to AuNPs stabilized with Glutamate-linker-2, we obtained exactly the same results as previously obtained with AuNPs stabilized with Glutamate-linker-1. Lysine-linker-1, Ornithine-linker-1 and Carnosine-linker-1 result in aggregation and after only few minutes of stirring the AuNPs precipitate in solution. However, Adding Aminoaacids-linker-2 to AuNPs stabilized with Glutamate-linker-2, surprisingly all thirteen modified amino acids were conjugated efficiently and no aggregation or AuNPs precipitation was observed. (Table 4)

TABLE 4

Double Conjugated AuNPs using stabilized AuNPs with Glutamate-linker-2.

| Metabolite | AuNPs-Glu-Linker 2 | |
|---|---|---|
| | Linker-1 | Linker-2 |
| Leucine | ✓ | ✓ |
| Isoleucine | ✓ | ✓ |
| Histidine | ✓ | ✓ |
| Carnosine | X | ✓ |
| Phenylalainine | ✓ | ✓ |
| Tyrosine | ✓ | ✓ |
| Valine | ✓ | ✓ |
| Glutamine | ✓ | ✓ |
| Aminoadipic Acid | ✓ | ✓ |
| Lysine | X | ✓ |
| Ornithine | X | ✓ |
| Alanine | ✓ | ✓ |

Checkmark means Stable dispersion.
X means aggregation.

Figure 14:
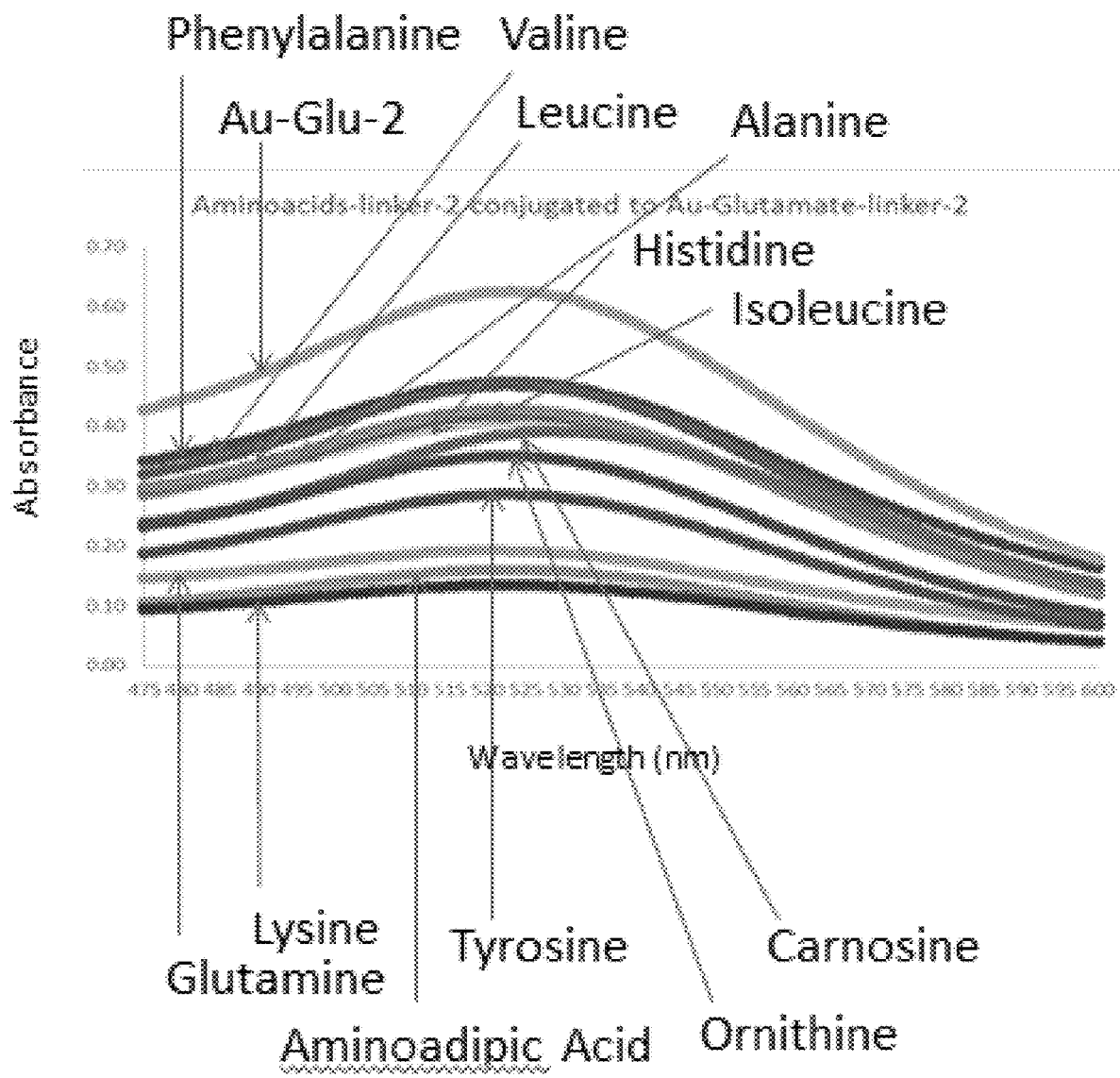
FIG. 14 shows UV-Vis Spectra of double conjugated AuNPs-Linker-2-Glutamate Using modified aminoacids with both linker-2.

FIG. 14 shows UV-Vis Spectra of double conjugated AuNPs-Linker-2-Glutamate using modified aminoacids with both linker-2

The contents of all reference listed herein are incorporated by reference.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

What is claimed is:

1. A water soluble heterobifunctional linker (L1), wherein said linker has the structure:

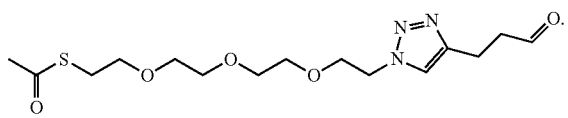 [SMILES: CC(=O)SCCOCCOCCOCCn1cc(CCC=O)nn1]

2. A water soluble heterobifunctional linker (L2), wherein said linker is has the structure:

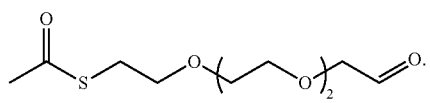

3. A compound of formula IIIA:

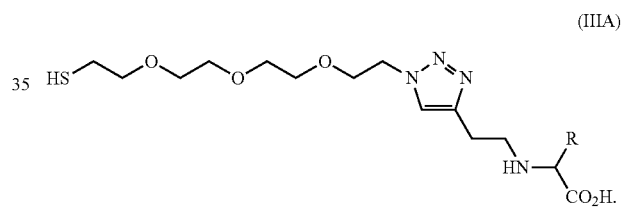

(IIIA)

wherein,
R is a side chain of a naturally occurring amino acid.

4. A compound of formula IIIB:

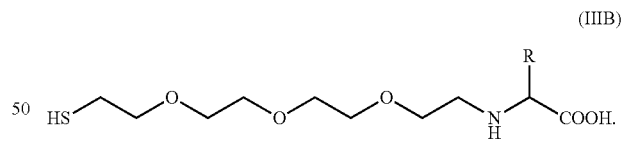

(IIIB)

wherein,
R is a side chain of a naturally occurring amino acid.

* * * * *